US006548254B2

(12) United States Patent
Beckman et al.

(10) Patent No.: US 6,548,254 B2
(45) Date of Patent: Apr. 15, 2003

(54) METHODS AND COMPOSITIONS FOR THE MANUFACTURE OF MOLECULAR BEACONS

(75) Inventors: Kenneth B. Beckman, Alameda, CA (US); Ricardo Mancebo, San Bruno, CA (US)

(73) Assignee: Gorilla Genomics, Inc., Alameda, CA (US)

( * ) Notice: Subject to any disclaimer, the term of this patent is extended or adjusted under 35 U.S.C. 154(b) by 0 days.

(21) Appl. No.: 09/844,710

(22) Filed: Apr. 27, 2001

(65) Prior Publication Data

US 2002/0009742 A1 Jan. 24, 2002

Related U.S. Application Data

(60) Provisional application No. 60/200,333, filed on Apr. 28, 2000.

(51) Int. Cl.[7] .......................... C12Q 1/68; C07H 21/04; C12P 19/34
(52) U.S. Cl. .......................... 435/6; 435/91.1; 536/23.1
(58) Field of Search .......................... 435/6, 91.1, 91.2, 435/810, 287.2, 288.7; 536/23.1

(56) References Cited

U.S. PATENT DOCUMENTS

| | | | |
|---|---|---|---|
| 5,057,410 A | * 10/1991 | Kawasaki et al. | ............. 435/6 |
| 6,037,130 A | 3/2000 | Tyagi et al. | |
| 6,103,476 A | * 8/2000 | Tyagi et al. | ................. 435/6 |
| 6,150,097 A | 11/2000 | Tyagi et al. | |
| 5,925,517 A1 | 7/2001 | Tyagi et al. | |

OTHER PUBLICATIONS

Blok and Kramer (1997) "Amplifiable hybridization probes containing a molecular switch" *Mol Cell Probes* 11:187–194.
Bonnet et al. (1999) "Thermodynamic basis of the chemical specificity of structured DNA probes" *Proc. Natl. Acad. Sci. U.S.A.* 96:6171–6176.
Fang et al. (1999) "Designing a novel molecular beacon for surface–immobilized DNA hybridization studies" *J. Am. Chem. Soc.* 121:2921–2922.
Hsuih et al. (1997) "Novel, ligation–dependent PCR assay for detection of hepatitis C in serum" *J CLin Microbiol* 34:501–507.
Kostrikis et al. (1998) "Molecular beacons: spectral genotyping of human alleles" *Science* 279:1228–1229.
Leone et al. (1995) "Molecular beacon probes combined with amplification by NASBA enable homogenous real–time detection of RNA." *Nucleic Acids Res.* 26:2150–2155.
Marras et al. (1999) "Multiplex detection of single–nucleotide variation molecular beacons" *Genet. Anal. Biomol. Eng.* 14:151–156.
Sokol et al. (1998) "Real time detection of DNA:RNA hybridization in living cells" *Proc. Natl. Acad. Sci. U.S.A.* 95:11538–11543.
Tygai et al. (1998) "Multicolor molecular beacons for allele discrimination" *Naure Biotechnology* 16:49–53.
Tyagi and Kramer (1996) "Molecular beacons: probes that fluoresce upon hybridization" *Nature Biotechnology* 14:303–308.
Vet et al. (1999) "Multiplex detection of four pathogenic retroviruses using molecular beacons" *Proc. Natl. Acad. Sci. U.S.A.* 96:6394–6399.

\* cited by examiner

*Primary Examiner*—Kenneth R. Horlick
(74) *Attorney, Agent, or Firm*—Jonathan Alan Quine; Quine Intellectual Property Law Group, P.C.

(57) ABSTRACT

Ligation-based assembly of oligonucleotides to produce molecular beacons is provided. Formation of molecular beacons is monitored to improve reaction yield and efficiency and to permit optimization of structurally similar molecular beacons. Ligation mixtures and libraries of molecular beacon components are also provided. Methods of detecting juxtaposed nucleic acids using modular molecular beacons such as intron-exon junctions are provided.

39 Claims, 30 Drawing Sheets

Fluorescein–5'–CGTCTGCT 3'–OH

OR

Dabsyl–5'–CGTCTGCT 3'–OH
(Oligo A)

Fig. 2

Dabsyl – 3' – GCAG – 5' – PO$_4$

OR

Fluorescein – 3' – GCAG – 5' – PO$_4$ (Oligo B)

Fig. 3

(Oligo A) Fluorescein–5'–CGTCTGCT 3'–OH
(Oligo B) Dabsyl –3'– GCAG 5'–PO$_4$

OR (Oligo A) Dabsyl –5'– CGTCTGCT 3'–OH
(Oligo B) Fluorescein –3'– GCAG 5'–PO$_4$

Fig. 4

F-5'-CGCCGC-3'-OH
(Oligo D)

Fig. 8

PO$_4$-5'-CGACG—GCGGCG-3'-Q (Oligo E)

Fig. 9

B-3'-GCGGCGGCTGC-5'

(Oligo F)

Oligo D → F-5'-CGCCGC

Fig. 17

Oligo H → TAGGCAACTCCAGTAGCGGCG-3'-Q

Fig. 18

Oligo F → B-3'-GCGGCGGCTGC-5'

Fig. 22

SEQUENCE LISTING

<160> NUMBER OF SEQ ID NOS: 14

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
ccccattcgg ggagca                                              16

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cgtctgctcc ccattcgggg agcagacg                                      28

<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cgacggcggc g                                                        11

<210> SEQ ID NO 4
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cgtcggcggc g                                                        11

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cgccgccgac ggcggcg                                                  17

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<221> NAME/KEY: modified_base
<222> LOCATION: (12)..(29)
<223> OTHER INFORMATION: A, T, C or G

<400> SEQUENCE: 6
cgccgccgac gnnnnnnnnn nnnnnnnnng cggcg                              35

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7

```
ccccattcgg ggagca                                                   16
```

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8

```
taggcaactc cagtagcggc g                                             21
```

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

```
cgacgtaact ctgaatcgcg c                                             21
```

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10

```
cgccgccgac gtaactctga atcgcgc                                       27
```

<210> SEQ ID NO 11
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11

```
gcctagcgcg a                                                        11
```

<210> SEQ ID NO 12
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12

```
cgacgtaact ctgaatcgcg ctaggcaact ccagtagcgg cg                      42
```

<210> SEQ ID NO 13
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13

```
cgccgccgac gtaactctga atcgcgctag gcaactccag tagcggcg                48
```

```
<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gtccgttaac attgagactt ttgaggtcat ccaagtagcc                              40
```

METHODS AND COMPOSITIONS FOR THE MANUFACTURE OF MOLECULAR BEACONS

CROSS REFERENCE TO RELATED APPLICATIONS

This application is a non-provisional of Application U.S. Ser. No. 60/200,333 filed Apr. 28, 2000. The present application claims priority to and benefit of this prior application, pursuant to 35 U.S.C. 119, as well as any other applicable statute or rule.

COPYRIGHT NOTIFICATION

Pursuant to 37 C.F.R. 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The present invention is in the field of molecular beacon synthesis and use for detection of target sequences, including juxtaposed sequences produced by splicing or cloning.

BACKGROUND OF THE INVENTION

Molecular beacons (MBs) are oligonucleotides designed for the detection and quantification of target nucleic acids (e.g., target DNAs). The basic principles of molecular beacon mediated target nucleic acid detection is depicted in FIG. 1.

As depicted, 5' and 3' termini of the MB collectively comprise a pair of moieties which confers detectable properties of the MB. As shown, one of the termini is attached to a fluorophore and the other is attached to a quencher molecule capable of quenching a fluorescent emission of the fluorophore. For example, one example fluorophore-quencher pair can use a fluorophore such as EDANS or fluorescein, e.g., on the 5'-end and a quencher such as Dabcyl, e.g., on the 3'-end.

When the MB is present free in solution, i.e., not hybridized to a second nucleic acid, the stem of the MB is stabilized by complementary base pairing. This self-complementary pairing results in a "hairpin loop" structure for the MB in which the fluorophore and the quenching moieties are proximal to one another. In this confirmation, the fluorescent moiety is quenched by the fluorophore.

The loop of the molecular beacon is complementary to a sequence to be detected in the target nucleic acid, such that hybridization of the loop to its complementary sequence in the target forces disassociation of the stem, thereby distancing the fluorophore and quencher from each other. This results in unquenching of the fluorophore, causing an increase in fluorescence of the MB.

Further details regarding standard methods of making and using MBs are well established in the literature and MBs are available from a number of commercial reagent sources. Further details regarding methods of MB manufacture and use are found, e.g., in Leone et al. (1995) "Molecular beacon probes combined with amplification by NASBA enable homogenous real-time detection of RNA." *Nucleic Acids Res.* 26:2150–2155; Tyagi and Kramer (1996) "Molecular beacons: probes that fluoresce upon hybridization" *Nature Biotechnology* 14:303–308; Blok and Kramer (1997) "Amplifiable hybridization probes containing a molecular switch" *Mol Cell Probes* 11:187–194; Hsuih et al. (1997) "Novel, ligation-dependent PCR assay for detection of hepatitis C in serum" *J Clin Microbiol* 34:501–507; Kostrikis et al. (1998) "Molecular beacons: spectral genotyping of human alleles" *Science* 279:1228–1229; Sokol et al. (1998) "Real time detection of DNA:RNA hybridization in living cells" *Proc. Natl. Acad. Sci. U.S.A.* 95:11538–11543; Tyagi et al. (1998) "Multicolor molecular beacons for allele discrimination" *Nature Biotechnology* 16:49–53; Bonnet et al. (1999) "Thermodynamic basis of the chemical specificity of structured DNA probes" *Proc. Natl. Acad. Sci. U.S.A.* 96:6171–6176; Fang et al. (1999) "Designing a novel molecular beacon for surface-immobilized DNA hybridization studies" *J. Am. Chem. Soc.* 121:2921–2922; Marras et al. (1999) "Multiplex detection of single-nucleotide variation using molecular beacons" *Genet. Anal. Biomol. Eng.* 14:151–156; and Vet et al. (1999) "Multiplex detection of four pathogenic retroviruses using molecular beacons" *Proc. Natl. Acad. Sci. U.S.A.* 96:6394–6399. Additional details regarding MB construction and use is found in the patent literature, e.g., U.S. Pat. No. 5,925,517 (Jul. 20, 1999) to Tyagi et al. entitled "Detectably labeled dual conformation oligonucleotide probes, assays and kits;" U.S. Pat. No. 6,150,097 to Tyagi et al (Nov. 21, 2000) entitled "Nucleic acid detection probes having non-FRET fluorescence quenching and kits and assays including such probes" and U.S. Pat. No. 6,037,130 to Tyagi et al (Mar. 14, 2000), entitled "Wavelength-shifting probes and primers and their use in assays and kits."

MBs are gaining wide spread acceptance as robust reagents for detecting and quantitating nucleic acids, including in real time (e.g., MBs can be used to detect targets as they are formed). A variety of commercial suppliers produce standard and custom molecular beacons, including Chruachem (chruachem.com), Oswel Research Products Ltd. (UK; oswel.com), Research Genetics (a division of Invitrogen, Huntsville Ala. (resgen.com)), the Midland Certified Reagent Company (Midland, Tex. mcrc.com) and Gorilla Genomics, LLC (Alameda, Calif.). A variety of kits which utilize molecular beacons are also commercially available, such as the Sentinel™ Molecular Beacon Allelic Discrimination Kits from Stratagene (La Jolla, Calif.) and various kits from Eurogentec SA (Belgium, eurogentec.com) and Isogen Bioscience BV (The Netherlands, isogen.com).

Despite such widespread acceptance and commercial development of MBs and related technologies, there remain a number of areas for improvement in the design, manufacture, synthesis, and purification of MBs. For example, in the area of single nucleotide polymorphism (SNP) detection, one typically designs, tests and synthesizes MBs separately for each SNP. This is, of course, inefficient and expensive at several levels. For example, the design and testing process is labor intensive. Additionally, it is difficult to scale the amount of MB actually needed to the synthesis scheme used to make the MB. That is, it can be difficult to scale a synthetic reaction down to produce only as much material as is actually needed—which, with the evolution of modern laboratory systems that run and detect reactions in nanoliter volumes, can be extremely small indeed.

Further in this regard, there are a number of specific difficulties with current synthetic schemes for making MBs. First, MB oligonucleotides require labels on both the 5' and 3' ends of the oligonucleotide. Adding 5' and 3' labels to oligonucleotides increases their cost dramatically, since specialized CPG (controlled pore glass) supports for solid-phase synthesis are typically used for the 3' attachment, and specialized phosphoramidites are required for the 5' attachment. Second, MBs are generally long oligonucleotides (typically greater than 30 nucleotides in length). The longer an oligonucleotide, the lower the percentage of final oligonucleotide product which is full-length, due to the compounding likelihood of synthesis failure at each base. Oligonucleotide purity, therefore, decreases as a function of oligonucleotide length, reducing the effectiveness of the MB and increasing the requirement for purification following synthesis. Indeed, typically, MB oligonucleotides are purified to operate according to specifications. Purification of oligonucleotides that differ by one or a few bases in length is best achieved by polyacrylamide gel electrophoresis (PAGE)-based methods, which are relatively labor intensive and, therefore, expensive. Finally, once designed and synthesized, there is a significant probability that a given MB will be ineffective, due to interfering secondary structure in its own loop region, or interfering secondary structure in the sequence of the target DNA to which the MB hybridizes, which interferes with the hybridization of the MB and target sequence.

The present invention uses modular synthesis strategies to overcome scalability, purification and synthesis issues noted above and to substantially decrease the amount of time needed to design and test MBs. Libraries, kits, devices, ligation mixtures and methods to achieve these goals are provided.

A fuller understanding of the invention will be provided by review of the following.

SUMMARY OF THE INVENTION

The present invention uses ligation-based assembly to make MBs. That is, MB components such as the stem, loop, label and label quenching moieties are made separately and then assembled by chemical or enzymatic ligation. Basic approaches include template-based, multiple template based and non-template based ligation assembly reactions. The MBs and components used to make the MBs can comprise nucleic acids, peptide nucleic acids, or both. Most typically, ligation dependent changes in label output are used to monitor ligation of MB components. Methods, devices, ligation mixtures and libraries are provided for high-throughput synthesis and ligation optimization.

Accordingly, the invention comprises methods of making one or more molecular beacon or molecular beacon component (a sub part of a complete molecular beacon). In the methods, a first oligonucleotide or peptide nucleic acid (PNA) corresponding to a first subsequence of a molecular beacon is provided (e.g., by synthesizing the component). At least a second oligonucleotide or PNA corresponding to a second subsequence of a molecular beacon is also provided (as set forth in more detail below, the MB can be made by ligation of 2 or more elements). The first and second oligonucleotides or PNAs are ligated together, thereby forming the molecular beacon (or the molecular beacon component, where the ligation scheme uses more than 2 oligonucleotides to make the MB). One or more additional oligonucleotide or PNA can also be included in the ligation reaction to produce the MB or MB component.

Most typically, the first oligonucleotide or PNA includes a label moiety and the second oligonucleotide includes a label quenching moiety. Common label moieties include those derived from Texas red, terbium chelate, europium cryptate, Fluorescein, IAEDANS, EDANS, BODIPY FL or the like. Common quenching moieties include TRITC (tetrarhodamine isothiocyanate), Allophycocyanin, EDANS, Tetramethylrhodamine, DABCYL, Fluorescein, BODIPY FL, QSY 7 dye or the like.

In a significant aspect, the method optionally includes monitoring a ligation-dependent change in a signal output of the molecular beacon, or of the first or second oligonucleotide or PNA. The ligation-dependent signal output is, e.g., a change in a fluorescence emission at a hybridization temperature that permits intra-molecular hybridization of the molecular beacon, but does not permit inter-molecular hybridization of the molecular beacon. The fluorescence emission change correlates to synthesis of the MB. Detection of this change can be used for a variety of purposes including optimizing one or more reaction parameters to increase yield of the molecular beacon or to improve the efficiency of the ligating step. Similarly, one or more reaction parameters can be optimized to minimize an amount of unligated material remaining following the ligating step.

Detection of the ligation-dependent change (i.e., formation of the MB from separate oligonucleotides) is dependent on the melting and self-annealing of any MB that is actually assembled. Thus, the invention optionally includes using melting and annealing profiles of ligation-dependent emission changes to identify one or more MBs that have an optimized structural component (loop or stem) sequence.

As noted, both template and non-template dependent ligation reactions can be used. For example, the first and second oligonucleotides or PNAs can be aligned on a template nucleic acid prior to said ligating step. The template oligonucleotide can participate in the ligation reaction (thus becoming part of the final MB) or can not participate in the reaction. In this later embodiment, the ends of the oligonucleotide or PNA can be structured to prevent ligation, e.g., in the case of an oligonucleotide by not including phosphate or hydroxyl groups at the terminus of the oligonucleotide. Most commonly, the template nucleic acid is a synthetic single-stranded oligonucleotide, though, e.g., PNAs or cloned nucleic acids can also be used to align MB components in the ligation reaction. Typically, the ligating step is performed via enzymatic ligation, though chemical ligation approaches can also be used. Common ligase enzymes suitable for the ligation reaction include Taq DNA ligase, *E. coli* DNA ligase, and T4 DNA ligase.

One advantage of the present invention is that purification of the MB from components used to make the MB is simplified due to the substantial difference in size between the MB and the oligos or PNAs used to make the MB. Thus, one aspect of the invention includes purifying the molecular beacon from one or more unligated first or second oligonucleotides or PNAs. Common purification methods include simple purification methods such as HPLC, ion-exchange chromatography or the like.

It will be appreciated from the foregoing that ligation mixtures, e.g., contained in device comprising detectors for monitoring ligation-dependent changes in MB signal output, as well as libraries of ligation components, e.g., used in the methods are also a feature of the invention. For example, ligation mixtures that include a first oligonucleotide or PNA comprising a label moiety, a second oligonucleotide or PNA comprising a quenching moiety that quenches the label moiety when placed proximal or in contact with the label moiety, a third oligonucleotide or PNA that is at least partly complementary to at least a portion of the first or second oligonucleotides, and a ligase are a feature of the invention. The first and second oligonucleotides or PNAs can also be at least partly complementary. Ligation of the first, second and third oligonucleotides or PNAs can result in formation of a molecular beacon, or the third oligo or PNA can simply be a template used in the ligation reaction (of course, additional oligos can be used as MB component elements, or as additional ligation templates). Thus, in one embodiment, ligation of the first and second oligonucleotides or PNAs results in formation of a molecular beacon with the third oligonucleotide providing a template for ligation of the first and second oligonucleotides. In another embodiment, nucleotides of the first and second oligonucleotides form at least a portion of a molecular beacon stem and nucleotides of the third oligonucleotide forms at least portion of a hairpin loop portion of the molecular beacon. These ligation mixtures can be formed in a device having a ligation reaction region, e.g., a micotiter tray, test-tube, cuvette, microfluidic component or other structure configured to receive the ligation reaction.

In the embodiments above, the second oligonucleotide or PNA is typically at least partly complementary to one or more target nucleic acid, e.g., at least partly complementary to one or more single nucleotide polymorphism (SNP). Thus, the MBs made according to the present invention can be used to detect a target nucleic acid such as a SNP, RNA, DNA or the like.

As noted above, a variety of label and quencher elements can be incorporated into the ligation mixture on either the PNA or oligonucleotide, including labels such as Texas red, terbium chelate, europium cryptate, Fluorescein, IAEDANS, EDANS, and BODIPY FL and quenchers such as TRITC (tetrarhodamine isothiocyanate), Allophycocyanin, EDANS, Tetramethylrhodamine, DABCYL, Fluorescein, BODIPY FL, and QSY 7 dyes. Again, ligases that can be used include $E.\ coli$ ligase, T4 ligase, Taq ligase and other known ligases. Ligation buffers, e.g., selected to facilitate operation of the ligase enzymes can be included as part of the mixture.

Kits comprising ligation mixture components (typically in unmixed form) and kit components (packaging materials, instructions for using the components to produce one or more molecular beacons, or one or more containers (microtiter trays, eppendorf tubes, etc.) for holding the components are also a feature of the invention. Standards for calibrating any MB detection reaction such as standard target sequences, amplification primers for amplifying a target sequence, or the like, can also be included in the kits of the invention.

One additional feature of the invention includes libraries of molecular beacon components. The libraries are designed, e.g., for the rapid synthesis of variants of an MB, e.g., to test variants against one or more target sequences. Such libraries include, e.g., a set of a plurality of hairpin loop oligonucleotides or PNAs, each of the plurality of hairpin loop oligonucleotides or PNAs comprising a subsequence of at least one molecular beacon, the subsequence comprising less than all of the molecular beacon, and at least one label or label quenching oligonucleotide or PNA. The oligonucleotide or PNA comprises at least one label or label quenching moiety, where ligation of at least one hairpin oligonucleotide or PNA and the label or label quenching oligonucleotide or PNA produces a molecular beacon or molecular beacon subsequence.

Most typically, the library is formatted in a gridded array, such as a microtiter tray, to facilitate access to the components of the library. However, any logically accessible arrangement can be used for the library. Thus, for example, individual members types of the hairpin loop oligonucleotides or PNAs are located in wells of the microtiter tray, with the other MB components being added to the wells for ligation to form MBs.

In one aspect, the hairpin loop oligonucleotide or PNA has a label or label quenching moiety, and ligation of the hairpin loop oligonucleotide or PNA to the label or label quenching oligonucleotide or PNA produces a molecular beacon. In another aspect, the library includes both a label oligonucleotide or PNA and a label quenching oligonucleotide or PNA, where ligation of the label oligonucleotide or PNA, the label quenching oligonucleotide or PNA and the hairpin loop oligonucleotide or PNA produces a molecular beacon.

The library can also include essentially any component of the ligation reaction described above, including enzymes, buffers, and the like. The libraries can also be made and used in kit form, e.g., providing the library in conjunction with packaging materials, instructions for using the library to produce one or more molecular beacons, one or more containers for holding one or more components of the library, one or more ligase enzyme, one or more standard target molecule, one or more amplification oligonucleotides, one or more ligation buffer, or the like.

In one embodiment, the invention provides methods for detecting juxtaposition of two or more target subsequences in a target nucleic acid, e.g., as occurs in RNA splicing (or RNA splicing and reverse transcription, as in cDNA production), cloning or the like. In this class of embodiments, a molecular beacon is formed by ligating a first oligonucleotide complementary to a first target subsequence and a second oligonucleotide complementary to a second target subsequence of the target nucleic acid. The resulting molecular beacon is hybridized to the target nucleic acid and a target-specific hybridization of the molecular beacon to the first and second subsequences is detected.

As noted above, a number of modular MB synthesis strategies are set forth herein. These typically include ligating the oligos that form the MB by aligning the oligonucleotides on one or more template and incubating the resulting hybridized set of oligonucleotides with a ligase. A MB used for juxtaposition detection can be formed from more than one oligo, i.e., one or more additional oligonucleotides can be ligated to the first and/or second oligonucleotides. For example, standard stem oligos comprising labels or label quenching moieties can be ligated.

BRIEF DESCRIPTION OF THE FIGURES

FIG. 2 is a schematic of a sequence of Oligo A.

FIG. 3 is a schematic of a sequence of Oligo B.

FIG. 4 is a schematic showing complementarity of Oligos A and B comprising a partial stem component of the example MB.

FIG. 8 is a schematic of a sequence of Oligo D.

FIG. 9 is a schematic of a sequence of Oligo E.

FIG. 10 is a schematic of a sequence of Oligo F.

FIG. 14 is a schematic of a more detailed view of a MB.

FIG. 17 is a schematic of a sequence of Oligo D.

FIG. 18 is a schematic of a sequence of Oligo H, and includes sequence complementary to a target (underline), and a template ligation sequence (double underline).

FIG. 22 is a schematic of a sequence of Oligo F.

DEFINITIONS

Figure 1:
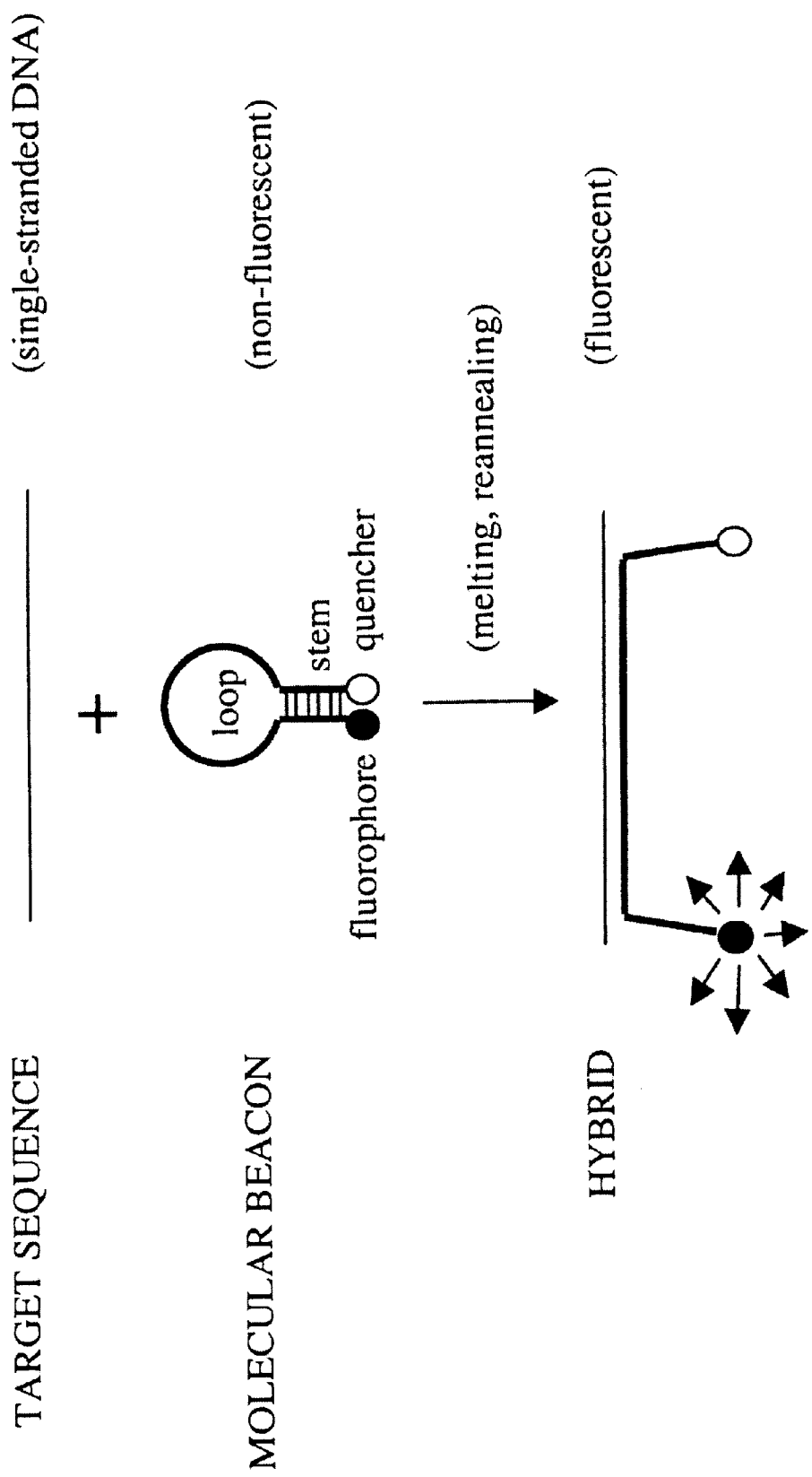
FIG. 1 is a schematic of a general scheme depicting hybridization of a MB to a target.

The following definitions supplement those in the art.

An "oligonucleotide" is a polymer of nucleotides. The polymer can additionally comprise non-nucleotide elements such as labels, quenchers, blocking groups, or the like. The nucleotides of the oligonucleotide can be natural or non-natural and can be substituted or modified.

A peptide nucleic acid (PNA) is a polymer of peptide nucleic acid monomers. The polymer can additionally comprise elements such as labels, quenchers, blocking groups, or the like. The monomers of the PNA can be substituted or modified. The term "nucleic acid" encompasses any physical string of monomer units that can be corresponded to a string of nucleotides, including a polymer of nucleotides, PNAs, modified oligonucleotides and the like.

A molecular beacon (MB) is an oligonucleotide or PNA which, under appropriate hybridization conditions, self-hybridizes to form a stem and loop structure. The MB has a label and a quencher at the termini of the oligonucleotide or PNA; thus, under conditions that permit intra-molecular hybridization, the label is typically quenched (or otherwise altered) by the quencher. Under conditions where the MB does not display intra-molecular hybridization (e.g., when bound to a target nucleic acid), the MB label is unquenched.

A "stem oligonucleotide" in the context of a MB is an oligonucleotide that includes nucleotides of an MB that are found in the MB stem. A "loop" or "hairpin loop" oligonucleotide is an oligonucleotide that includes nucleotides of an MB that are found in the loop portion of the MB. Similarly, a stem PNA includes monomers of a PNA MB that are found in the MB stem. A "loop" or "hairpin loop" PNA is a PNA that includes monomers of a PNA MB that are found in the loop portion of the MB.

A label is a moiety that facilitates detection of a molecule. Common labels in the context of the present invention include fluorescent and calorimetric labels.

A quencher is a moiety that alters a property of the label when it is in proximity to the label. Both FRET and non-FRET based quenchers are appropriate to the present invention. The quencher can actually quench an emission, but it does not have to, i.e., it can simply alter some detectable property of the label, or, when proximal to the label, cause a different detectable property than when not proximal to the label.

A "library" is at least one set of physical components (e.g., MBs, MB component oligos, etc.), having two or more elements. The library can include additional components (ligation mixtures, etc.) as well.

DETAILED DISCUSSION

The invention described herein provides a simplified approach to making MBs. In particular, this disclosure describes methods, compositions, devices and libraries for rapidly and inexpensively generating molecular beacons in a high-throughput fashion and for generating and testing sets of MBs against one or more target of interest.

In particular, methods of assembling MBs from shorter oligonucleotides are described. The methods involve ligating the shorter oligonucleotides to form the components of the MB, i.e., sequences which form the stem-loop structure and which have appropriate quencher and fluorophore components. Two example approaches are described in some detail below, i.e., a template-independent ligation approach and a template mediated ligation approach.

In the template-independent ligation approach, the MB is formed by ligation of 3 (or more) component oligonucleotides: a first oligo that comprises a fluorophore and a sequence which forms a portion of the stem structure; a second oligonucleotide that comprises a quenching moiety; a portion of the stem structure and a third sequence which forms a portion of the stem structure and a portion of the hairpin structure. This approach allows batch production of the first and second oligonucleotides, with only the third oligonucleotide (which includes the portion of the MB which is specific for a target of interest) being custom synthesized (of course, this target complementary sequence can also be made from multiple oligos, and examples of such approaches are provided below). In addition, because the unligated components are much smaller than the fully ligated MB, purification of the final product MB is considerably simplified. Indeed, less purification of the components is also needed, because the ligation reaction itself selects against ligation of incomplete component oligonucleotides.

In the template-mediated assembly approach, the M is formed by ligation of two (or optionally more) oligos, which are aligned on one or more standard template oligonucleotide(s) to place the 3' and 5' ends of the two oligos into proximity for the ligation reaction to occur. The first oligonucleotide (and/or additional oligonucleotides, if additional oligos are involved in the ligation to be performed) and the template oligonucleotide(s) can be batch synthesized, with only the second oligonucleotide (which includes the portion of the MB which is specific for a target of interest) being custom made (as is noted in more detail below, target regions can be broken into more than one oligo; thus, more than one oligo can be custom synthesized, depending on the exact format at issue). Here again, the alignment/ligation portion of the synthesis helps prevent incomplete MB synthesis, reducing the need for purification of the component elements of the MB. Furthermore, as with the preceding approach, final purification of the MB from its component elements is simplified by the substantial size difference between the MB and the oligos used to synthesize the MB.

With either of these approaches it is, of course, possible to further logically fragment the MB, i.e., to use more than 2 or 3 oligos in the synthesis of the MB. For example, one could align 3, 4, or even more oligos on one or more template oligo(s), allowing ligase to join multiple oligos on the template(s). However, such additional oligos are not necessary. Similarly, a template-independent ligation approach can be combined with the template-mediated ligation approach to create MBs or component elements of the MBs, though, again, this is not necessary.

The following section describes the basic approaches in more detail. One of skill will recognize a variety of features and components that can be substituted to achieve similar results.

LIGATION-BASED MB SYNTHESIS

Template-Independent Ligation

One basic class of embodiments is illustrated in FIGS. 2–7, involving the steps described therein and below. The sequences shown in the Figures are meant to be for illustration of the principle only, not to limit the application to the illustrated concepts. Any sequences which satisfy basic complementarity principles can be substituted.

As illustrated, a first short oligonucleotide is synthesized with a fluorophore (or quencher) molecule attached to its 5' end, by conventional methods of DNA synthesis as known by those skilled in the art ("Oligo A," FIG. 2).

A second oligonucleotide is synthesized with a quencher (or fluorophore) attached to its 3' end, and also bearing a 5' phosphate group, also by conventional methods of DNA synthesis as known by those skilled in the art ("Oligo B," FIG. 3).

Oligonucleotides A and B are designed such that they are self-complementary and form a partial stem of a MB, as illustrated in FIG. 4, in such a way that the fluorophore and quencher molecule are situated at the blunt end of the double-stranded stem, to minimize the distance between the two molecules and thereby maximize the quenching of the fluorophore by the quencher. Furthermore, oligonucleotides A and B are designed such that one of the two oligonucleotides has an overhang great enough to permit hybridization of a third oligonucleotide, oligonucleotide C, as described below.

Figure 5:
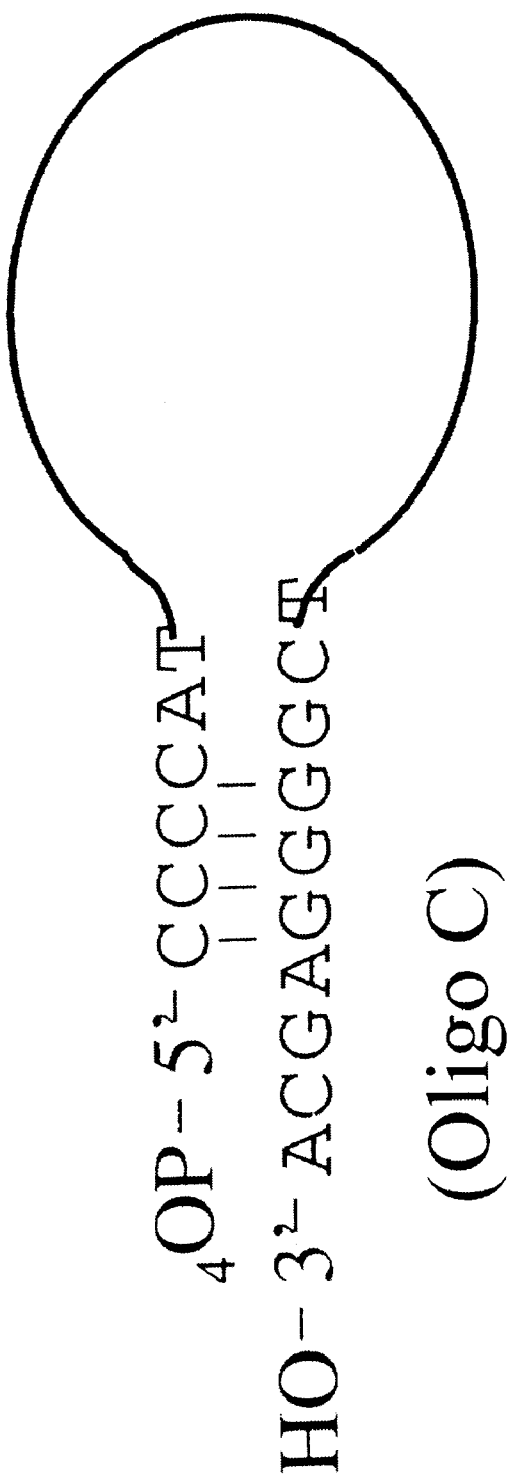
FIG. 5 is a schematic of a sequence of Oligo C showing the partial stem and loop structure of a MB component of the example MB.
Figure 6:
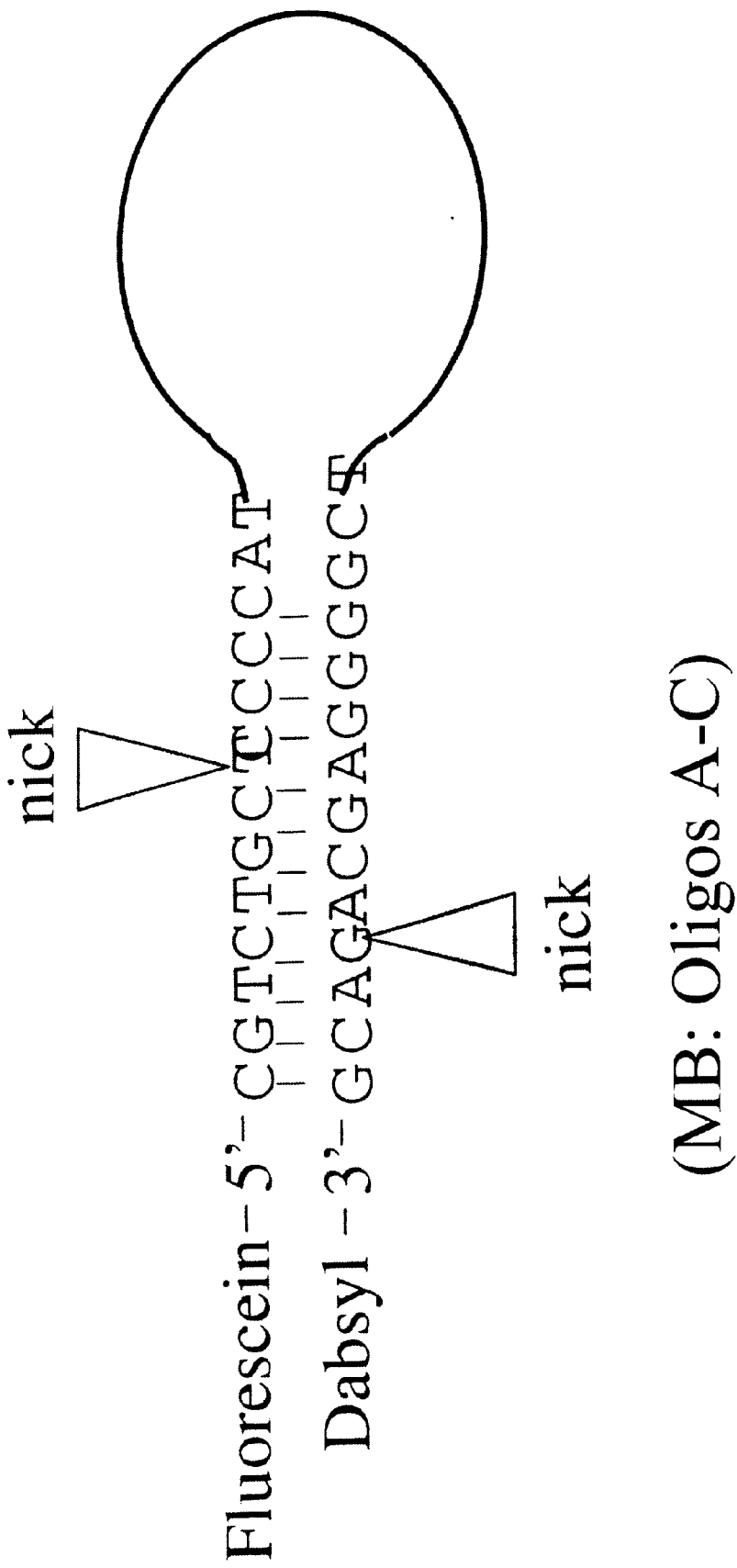
FIG. 6 is a schematic of an annealing of Oligos A, B and C.

A third oligonucleotide is synthesized which comprises the loop and part of the stem of the MB, which bears a 5' phosphate group, by conventional methods of DNA synthesis ("Oligo C," FIG. 5). Oligo C is also designed to have an overhang which is complementary to the overhang of the Oligo A: Oligo B duplex, such that the three oligonucleotides together form the hybridized structure illustrated in FIG. 6, in which a junction between the two double-stranded regions positions the 5' phosphate group of Oligo B immediately adjacent to the 3' hydroxyl group of Oligo C, and positions the 5' phosphate group of Oligo C immediately adjacent to the 3' hydroxyl group of Oligo A. In this orientation, the three oligonucleotides can be ligated into a single oligonucleotide MB. A variation of the synthesis of Oligo C which does not require the addition of a 5' phosphate group to the oligonucleotide is to make a longer sequence which contains a self-complementary stem structure with a site for a restriction enzyme, which is then digested to generate the desired complementary overhang.

Figure 7:
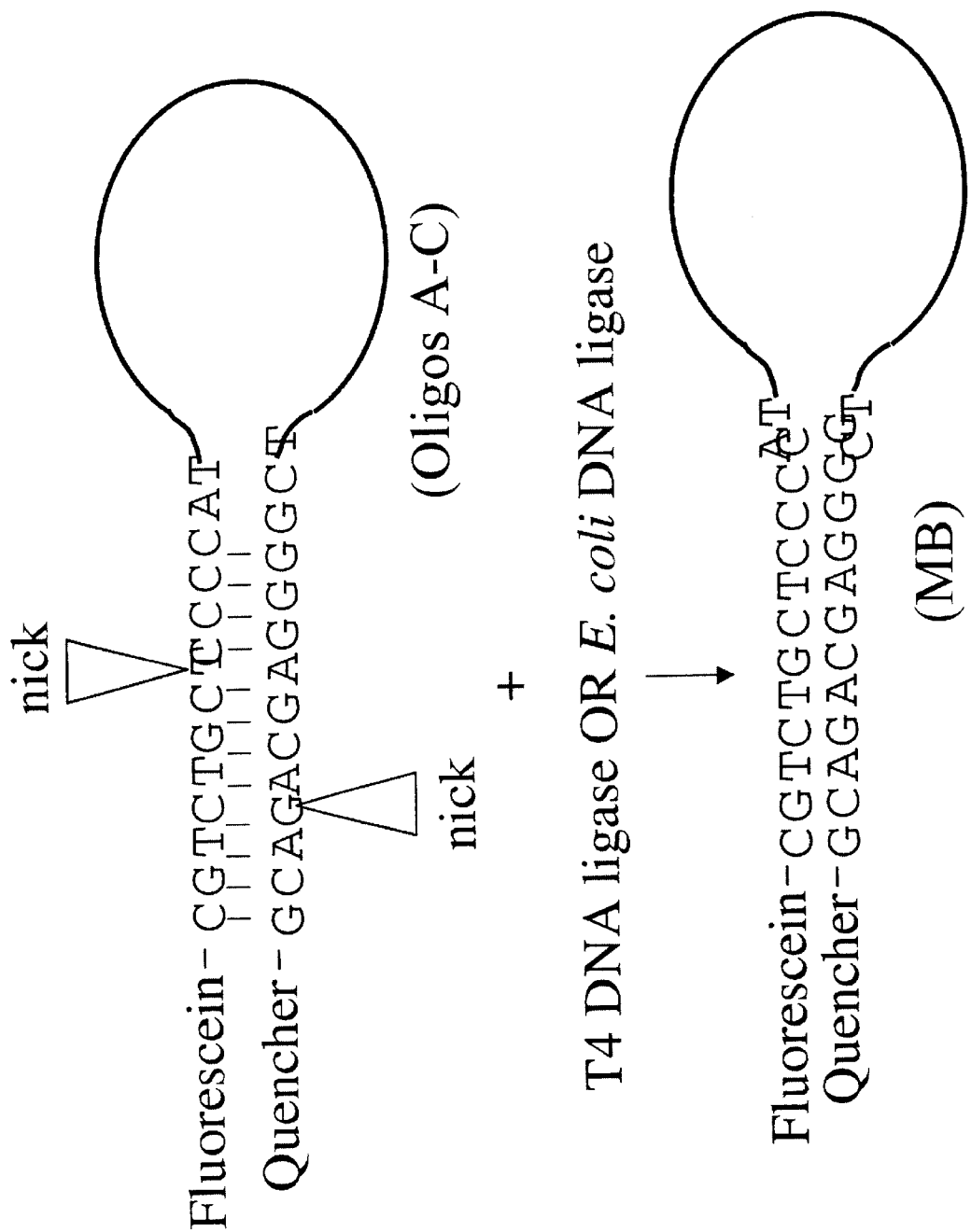
FIG. 7 is a schematic of a ligation of Oligos A, B and C.

Enzymatic ligation, using an enzyme such as T4 ligase, *E. coli* ligase, a thermostable ligase, or any other enzyme capable of ligating nicks in double-stranded DNA molecule, is then used to convert the hybridized structure composed of Oligo A, Oligo B, and Oligo C into a single oligonucleotide (Oligo A-C-B), as shown in FIG. 7. Temperatures and salt concentrations of the ligation reaction are maintained such that the complementary overhangs are kept in close proximity. Ligation conditions can be manipulated in various well-known ways for maximizing the efficiency of the reaction.

Lastly, the ligated structure Oligo A-C-B is purified away from the individual components, which is easily achieved due to its greater length. Purification can be achieved either by reverse-phase HPLC, or by many other means, including gel filtration, ion exchange chromatography, or by other means known to those skilled in the art.

Advantages of this class of embodiments include the following.

First, Oligo A and Oligo B, possessing fluorophore and quencher molecules, need only be made once, as they can be used in the manufacture of numerous different MBs, which will differ only in the sequence of Oligo C. As long as Oligo C always possesses an overhang which is complementary to the overhang of Oligo A: Oligo B, the expense of synthetically adding 3' and 5' labels to each MB can be avoided. Second, purification of MBs is simplified by the fact that the final product A-C-B is considerably longer than A, B, or C alone. In other words, in any chromatographic purification, the separation of the desired product will be straightforward and PAGE-based separation is not necessary to produce highly pure MBs. Oligos A and B need only be purified once, and they can be made in a relatively large batch (which simplifies purification). Moreover, many of the n-1 and other incomplete versions of Oligo C do not have an appropriate overhang for hybridization and ligation, and, therefore, are not incorporated into the MB. Third, the simplicity and low cost of the method provides for the affordable generation of MBs in a high-throughput (e.g., 96 or 384 (or greater number) well microtiter tray, or even microfluidic) format. Fourth, high-throughput assembly of MBs allows multiple MBs to be generated and tested as hybridization probes for a given target sequence (e.g., for SNP discrimination).

Template-Mediated Ligation

Figure 11:
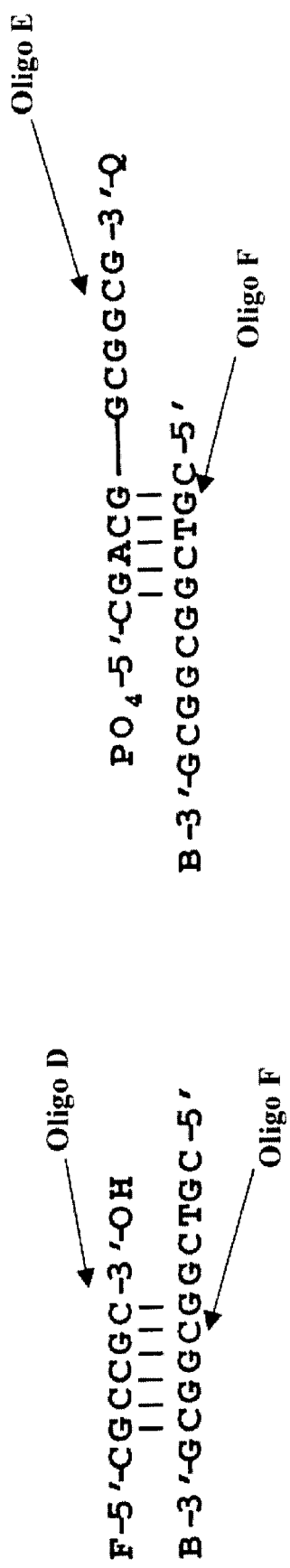
FIG. 11 is a schematic showing complementarity of Oligos D and F and Oligos E and F comprising partial components of the example MB.

In a second class of embodiments which utilizes a template for MB assembly, a first short oligonucleotide is synthesized with a fluorophore molecule attached to its 5' end, again, by conventional methods of DNA synthesis ("Oligo D", see FIG. 8). Again, an exact sequence shown is for illustrative purposes, but could be entirely different. Oligo D will, however, be complementary to Oligo F as shown in FIG. 11. In FIG. 8, the fluorophore is indicated as "F." In the final product MB, the oligo sequence comprises all or part of one half of the beacon's "stem" sequence. The sequences shown here, which are complementary to Oligo F, are 6 nucleotides (nt) in length, but could be as short as about 4 nt or as long as about 10 nt, and still effectively anneal to a complementary Oligo F.

Figure 9:
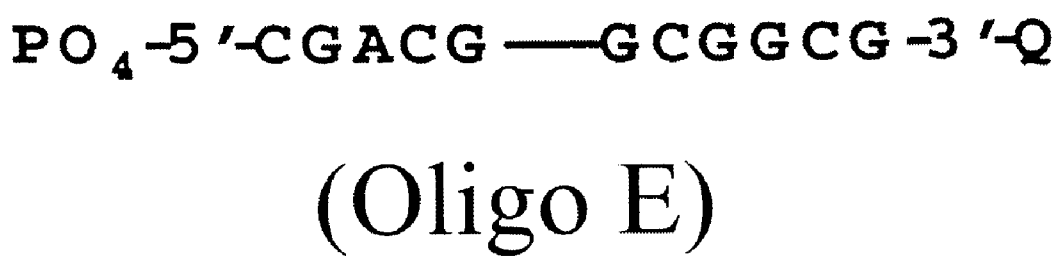

A second oligonucleotide is synthesized with a quencher attached to its 3' end, and also bearing a 5' phosphate group, by conventional methods of DNA synthesis as known by those skilled in the art ("Oligo E", FIG. 9). This second oligo also includes a target-specific sequence which becomes the "loop" of the molecular beacon. Again, the exact sequence shown is for illustrative purposes, and could be different, but is complementary to Oligo F as shown in FIG. 11. The quencher is indicated as "Q." The region indicated by the line in the middle of the sequence indicates the variable loop region of the beacon, which is typically in the range of 17 to 25 nucleotides in length, but can be shorter or longer. The region 3' to the variable loop region comprises all of part of one half of the MB "stem" sequence, and is complementary to Oligo D. The region 5' to the variable loop region is complementary to Oligo F. The sequence shown in this example is 5 nt in length, but can be as short as 4 nt or as long as 10 nt, and still effectively anneal to a complementary Oligo F.

Figure 13:
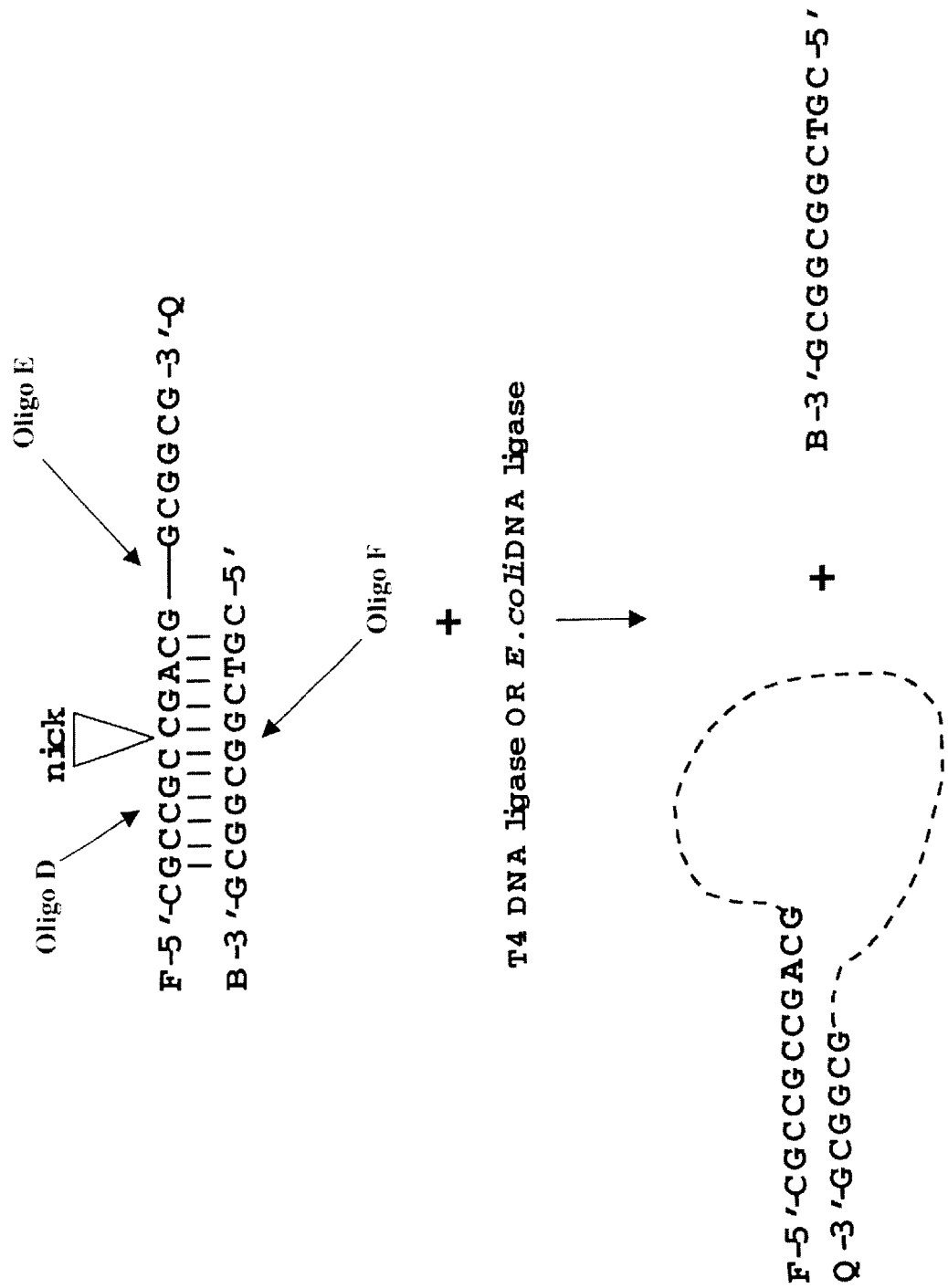
FIG. 13 is a schematic of the conversion of the hybridized three oligo structure in FIG. 12 into a MB.
Figure 14:
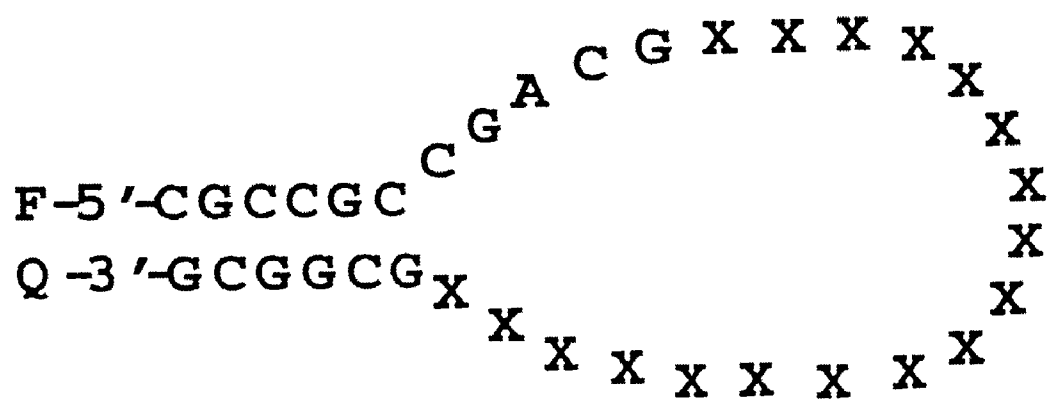

Oligonucleotides D and E are designed such that they form a self-complementary hybrid at their 5' (Oligo D) and 3' (Oligo E) ends, which form the stem of the MB, as illustrated in FIGS. 13 and 14, in such a way that the fluorophore and quencher molecule are situated at the blunt end of the double-stranded stem, to minimize the distance between the two molecules and thereby maximize the quenching of the fluorophore by the quencher. Furthermore, oligonucleotides D and E are designed such that they are both complementary to a third "ligation template oligo (Oligo F).

A third oligonucleotide (the ligation template oligonucleotide) is synthesized which bears a blocked 3' end, by conventional methods of DNA synthesis ("Oligo F", FIG. 10). Again, an exact sequence shown is for illustrative purposes, but could be different, as long as it is appropriately complementary to Oligos D and E as shown in FIG. 11. The ligation template oligo is blocked at its 3' end so that it can not take part in ligation reactions. Such 3' blockages include (for example) 3' phosphate group addition, or the use of a dideoxynucleotide as the 3' nucleotide in the sequence.

Figure 12:
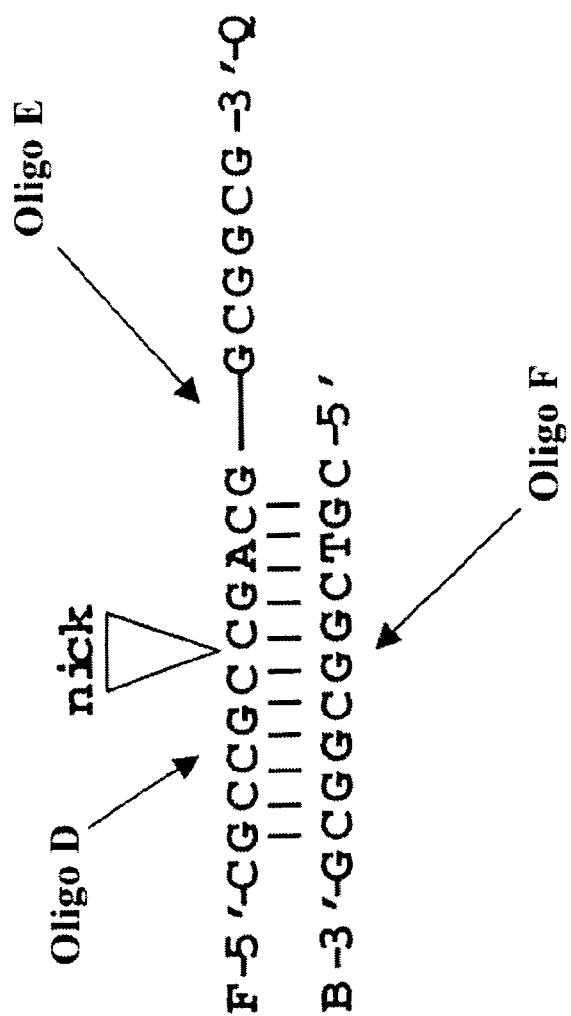
FIG. 12 is a schematic showing hybridization of Oligos D–F.

Oligo F is designed to form a duplex with both Oligo D and Oligo E, such that the three oligonucleotides together form the hybridized structure illustrated in FIGS. 11–12. As illustrated, the oligonucleotides form a duplex, with Oligo F acting as a template for ligation of Oligos D and E. The hybridization is performed at an appropriate stringency to provide for specific hybridization of the oligos. The hybridization can be performed with a large excess of Oligo F to provide for the trimolecular hybrid which competes favorably against any bimolecular hybridization between any complementary regions of Oligos D and E.

As shown, upon hybridization, a junction forms between two double-stranded regions, which positions the 5' phosphate group of Oligo E immediately adjacent to the 3' hydroxyl group of Oligo D. In this orientation, Oligo D and Oligo E can be ligated into a single oligonucleotide MB.

As noted above, the 3' blockage of Oligo F can be achieved by various methods, such as the addition of a 3' phosphate group or the use of a 3' dideoxynucleotide. The functional use of such a blockage is simply that it prevents Oligo F from taking part in any ligation reactions. Oligo F also can be synthesized not to carry a 5' phosphate group, and, therefore, not to take part in ligation reactions with its 5' end.

Enzymatic ligation, using an enzyme such as T4 ligase, *E. coli* ligase, a thermostable ligase, or any other enzyme capable of ligating nicks in a double-stranded DNA molecule, is used to convert the hybridized structure composed of Oligo D, Oligo E, and Oligo F into two oligonucleotides (Oligo D-E and the "ligation template oligo" Oligo F), as shown in FIG. 13 and FIG. 14. Temperatures and salt concentrations of the ligation reaction are maintained such that the complementary overhangs are kept in close proximity. Conditions of ligation can be manipulated in various ways known to those skilled in the art for maximizing the efficiency of the reaction.

As depicted, FIG. 14 provides a detailed view of the MB shown in FIG. 13. The dashed lines from previous figures is here shown as the letter X, which represents any of the bases G, C, A, or T. The loop of the molecular beacons generated by this method therefore include both the target-specific region (illustrated by the X's) as well as a region which may not be target-specific (in this example, the sequence CGACG, having been added for the purposes of effecting ligation of Oligo D to Oligo E.

Lastly, the ligated structure Oligo D-E is purified away from any individual unligated components, and Oligo F, which is easily achieved due to its substantially greater length. Purification can be achieved, e.g., by reverse-phase HPLC, or by many other method, including gel filtration, ion exchange chromatography, or by any other available method.

Advantages of this embodiment include the following.

First, Oligo D (which includes a fluorophore) can be made once and used in the manufacture of numerous different MBs, which differ only in the sequence of the variable loop region of Oligo E (the part of the MB which provides target specificity). The expense of adding 5' labels to each MB can, thus, be avoided.

Second, purification of product MBs is simplified by the fact that the final product oligo D-E is considerably longer than D, E, or F alone. In other words, in any chromatographic or other simple purification, the separation of the desired product is straightforward. Oligo D need only be purified once, since it can be made in a large batch. Moreover, many of the "failure" sequences ("n–1" and shorter sequences) of Oligo E do not have an appropriate 5' phosphate group and complementary region for ligation to Oligo D and, therefore, are eliminated from any product MB. Third, the simplicity and low cost of the method provides for the affordable generation of MBs in a high-throughput (e.g., microtiter or microfluidic) format. The benefit of such a method is that by generating multiple MBs for each sequence to be analyzed, it is possible to determine which MBs work as effective hybridization probes, facilitating the use of MBs.

MONITORING MB SYNTHESIS IN A TEMPLATE-INDEPENDENT LIGATION REACTION

The reagents and reactions illustrated in FIGS. 2–7 show a method for the modular assembly of MBs by enzymatic ligation as discussed in detail above. The yield from ligation-based MB synthesis is directly related to the efficiency of the ligation reaction. As the efficiency of the reaction increases, the overall yield also increases. Monitoring the efficiency of each MB synthesis reaction can be done to optimize conditions of enzymatic ligation synthesis of MB. The following discussion provides methods for directly monitoring ligation-based MB syntheses.

Figure 15:
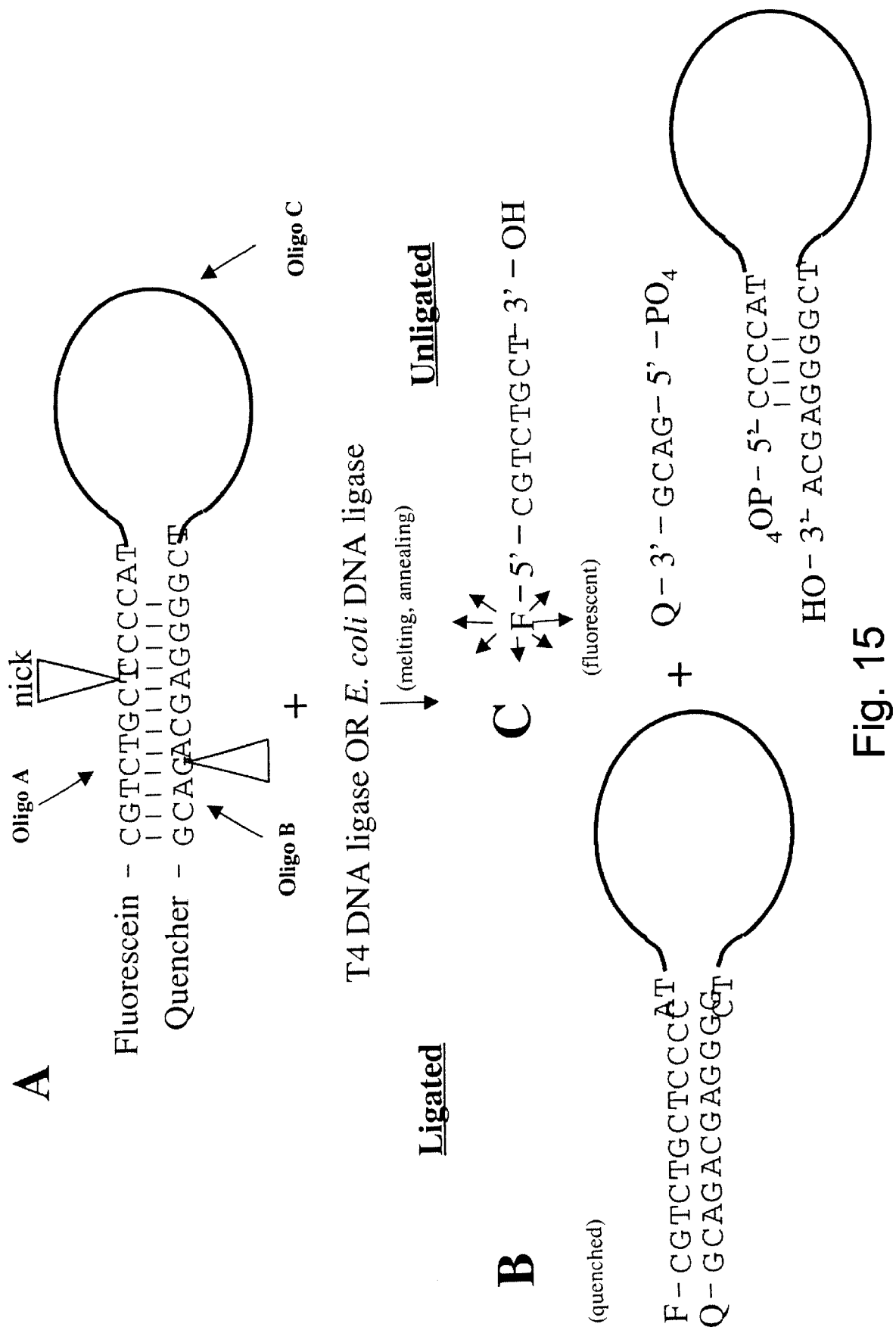
FIGS. 15A–B provide a schematic of a detection method for monitoring MB formation in a template-independent ligation reaction.

Illustrated in FIG. 15, Panel A are three annealed oligonucleotides labeled Oligo A, Oligo B, and Oligo C. A full-length molecular beacon is synthesized by the enzymatic ligation of the annealed component oligonucleotides, as shown in FIG. 15, Panel B. As the efficiency of the ligation reaction increases, the percentage of the ligated product shown in FIG. 15, Panel B also increases, and the percentage of unligated component molecules shown in FIG. 15, Panel C decreases. The annealing is performed at an optimal stringency to provide for specific self-annealing of the MB.

Melting and annealing of enzymatic ligation reactions using optimized conditions yield the ligated MB that is quenched, as shown in FIG. 15, Panel B. Melting and annealing of enzymatic ligation reactions using optimized conditions also yields the unligated fluorophore-conjugate that fluoresces, shown in FIG. 15, Panel C. The total amount of fluorescent emission is therefore related to the amount of fluorophore-conjugate that is unligated. The efficiency of the ligation reaction then can be determined by monitoring the incorporation of the fluorescent unligated conjugate into the quenched ligated MB, incorporation is detected as a reduction in fluorescent emission.

Advantages of this approach are several. First, optimization of ligation conditions permits product yields to be maximized. Second, maximizing product yields reduces the amount of unused label from each reaction. Third, monitoring MB synthesis reactions by melting and annealing reactions can be used to identify molecular beacons that have optimal loop sequences. Fourth, the identification of optimal loop sequences within MBs can be used in the overall design of molecular beacons.

MONITORING MB SYNTHESIS IN A TEMPLATE-MEDIATED LIGATION REACTION

The reagents and reactions illustrated in FIGS. 8–13 show a method for the modular assembly of MBs by enzymatic ligation. The yield from ligation-based MB synthesis is directly related to the efficiency of the ligation reaction. As the efficiency of the reaction increases, the overall yield also increases. Monitoring the efficiency of each MB synthesis reaction can be done to optimize conditions for each enzymatic ligation. Discussed below is a method for directly monitoring ligation-based MB syntheses.

Figure 16:
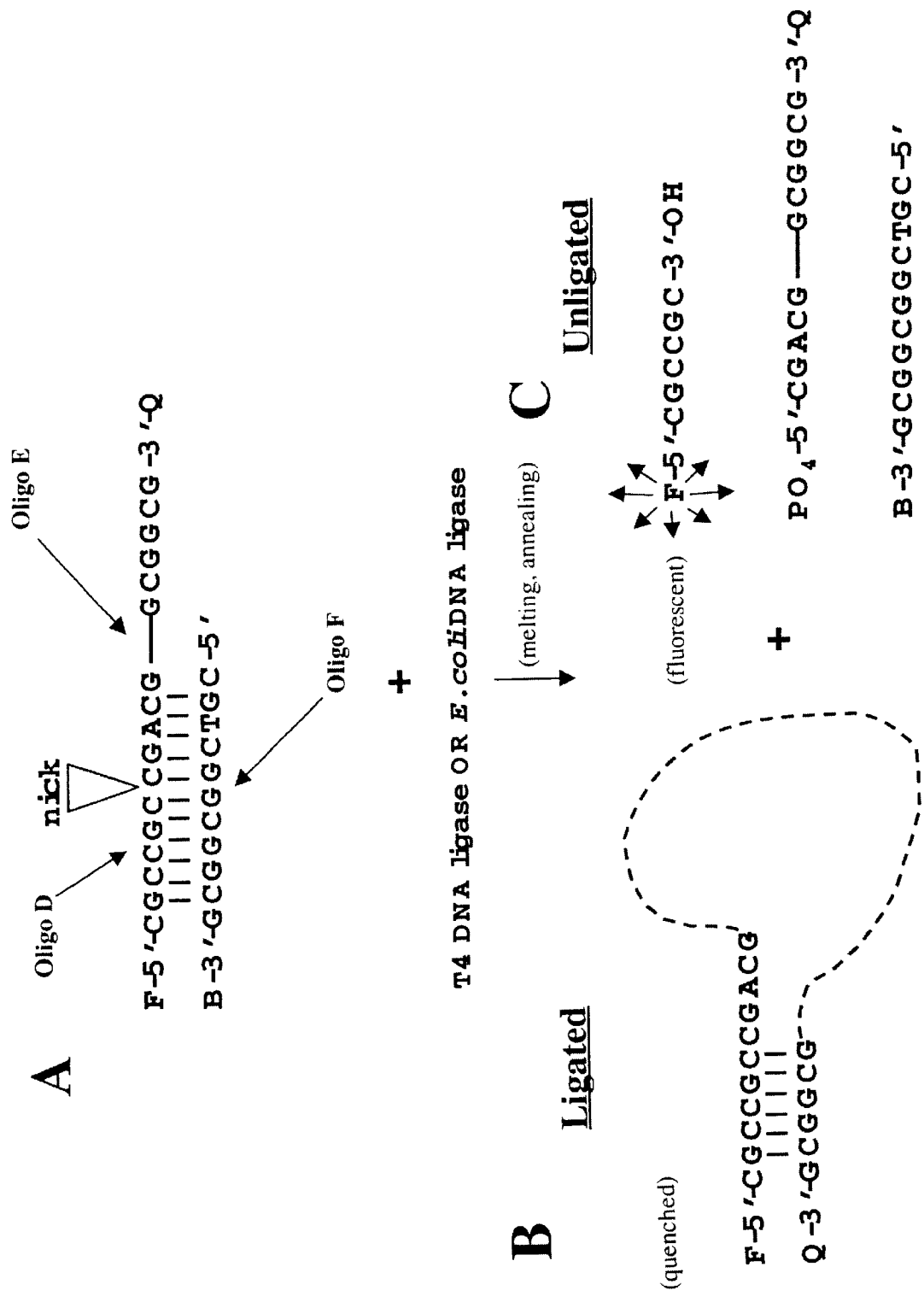
FIGS. 16A–C provide a schematic detailing a detection method for monitoring MB formation in a template-independent ligation reaction.

Illustrated in FIG. 16, Panel A are three annealed oligonucleotides labeled Oligo D, Oligo E, and Oligo F. A full-length molecular beacon is synthesized by enzymatic ligation of the annealed component oligonucleotides, as shown in FIG. 16, Panel B. As the efficiency of the ligation reaction increases, the percentage of the ligated product shown in FIG. 16, Panel B also increases, and the percentage of unligated component molecules shown in FIG. 16, Panel C decreases. The annealing is performed at an optimal stringency to provide for specific self-annealing of the MB.

Melting and annealing of enzymatic ligation reactions using optimized conditions yield the ligated MB that is quenched, shown in FIG. 16, Panel B. Melting and annealing of enzymatic ligation reactions using optimized conditions also yield the unligated fluorophore-conjugate that fluoresces, shown in FIG. 16, Panel C. The total amount of fluorescent emission is therefore related to the amount of fluorophore-conjugate that is unligated. The efficiency of the ligation reaction then can be determined by monitoring the consumption of the fluorescent unligated conjugate into the quenched ligated MB. Consumption is detected as a reduction in fluorescent emission.

Advantages of this approach are also several. First, optimization of ligation conditions permits product yields to be maximized. Second, maximizing product amounts/yields reduces the amount of unused label from each reaction. Third, monitoring MB synthesis reactions by monitoring melting and annealing reactions can be used to identify molecular beacons that have optimal loop sequences. Fourth, the identification of optimal loop sequences within MBs can be used in the overall design of molecular beacons.

DETECTION OF COMPOSITE JUNCTION SEQUENCES

In a third class of embodiments which utilizes multiple templates for MB assembly, a loop structure is assembled that is comprised of a central region containing template ligation sequence, and two (or more) flanking regions containing sequences complementary to composite junction sequences. This class of embodiments is illustrated in FIGS. 17–29, involving the steps described therein and below. The sequences shown in the Figures are meant to be for illustration of the principle only, not to limit the application to the illustrated examples. Any sequences which satisfy basic complementarity principles can be substituted. Further, any sequence that is a composite of two or more sequences can be usefully detected by the methods of this example.

Figure 17:
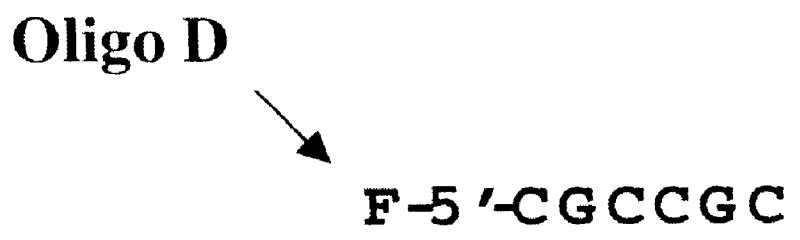

A first short Oligonucleotide is synthesized with a fluorophore molecule attached to its 5' end, by conventional methods of DNA synthesis as known by those skilled in the art ("Oligo D," see, FIG. 17).

Figure 18:
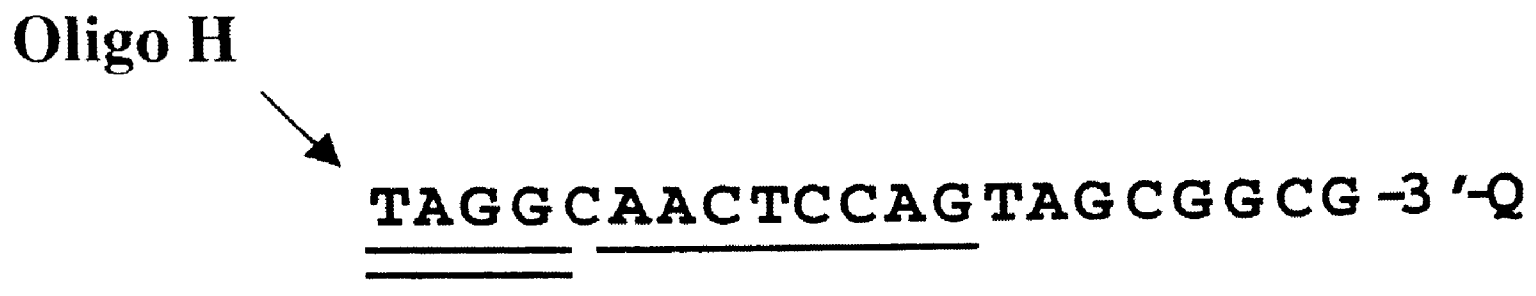

A second Oligonucleotide is synthesized with a quencher attached to its 3' end, and also bearing a 5' phosphate group, by conventional methods of DNA synthesis as known by those skilled in the art ("Oligo H," see, FIG. 18). This second Oligo would also include a target-specific sequence which would become part of the "loop" (underline) of the molecular beacon, and a sequence for template-dependent ligation (double underline).

Figure 19:
FIG. 19 is a schematic of a sequence of Oligo G, and includes sequence complementary to a target (underline), and a template ligation sequence (double underline).

A third Oligonucleotide is synthesized bearing a 5' phosphate group by conventional methods of DNA synthesis ("Oligo G," see, FIG. 19). This third Oligo includes a target-specific sequence which becomes part of a "loop" (underlined sequence) of the molecular beacon, and a sequence for template-dependent ligation (double underline).

Figure 20:
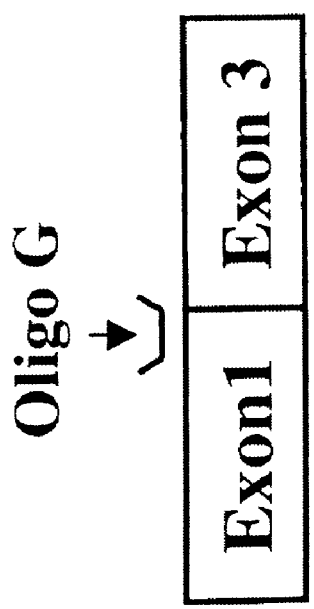
FIG. 20 is a schematic of Oligo G annealing to a sequence in exon 1 that is 5' to a splice junction.

Oligonucleotide G is designed such that it is complementary to sequences 5' to a splice junction that results from an alternative splicing event that joins exons 1 and 3, as illustrated in FIG. 20.

Figure 21:
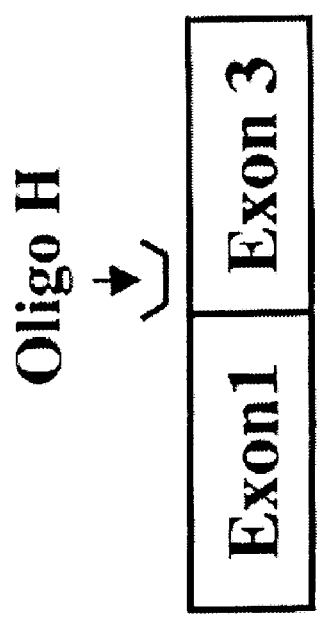
FIG. 21 is a schematic of Oligo H annealing to a sequence in exon 3 that is 3' to a splice junction.
Figure 23:
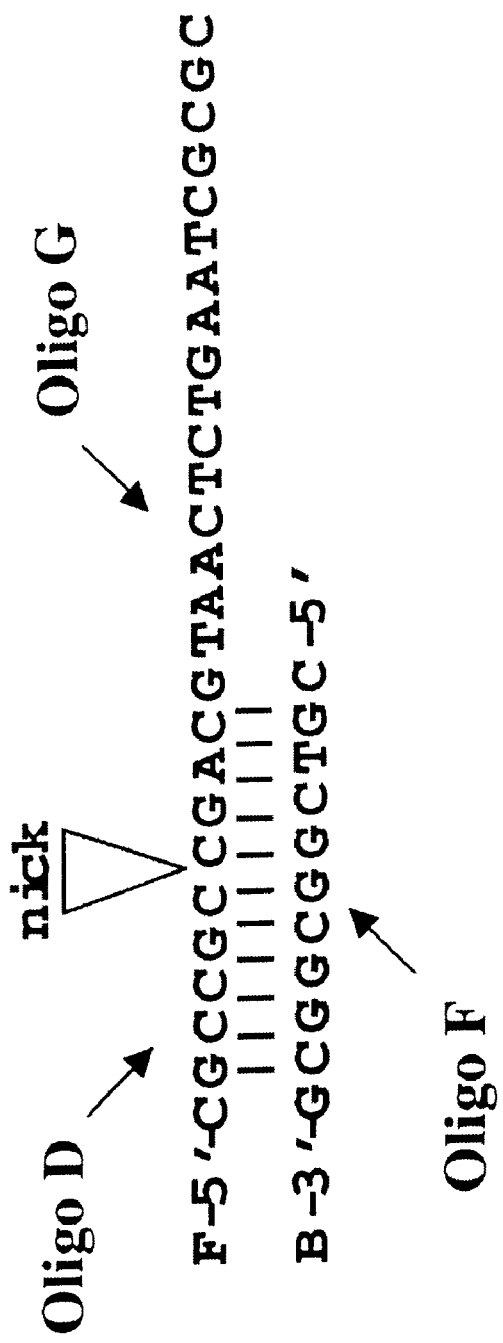
FIG. 23 is a schematic showing hybridization of Oligos D, G and F, comprising partial components and a ligation template for the assembly of the example MB.

Oligonucleotide H is designed such that it is complementary to sequences 3' to a splice junction that results from an alternative splicing event that joins exons 1 and 3, as illustrated in FIG. 21.

Figure 22:
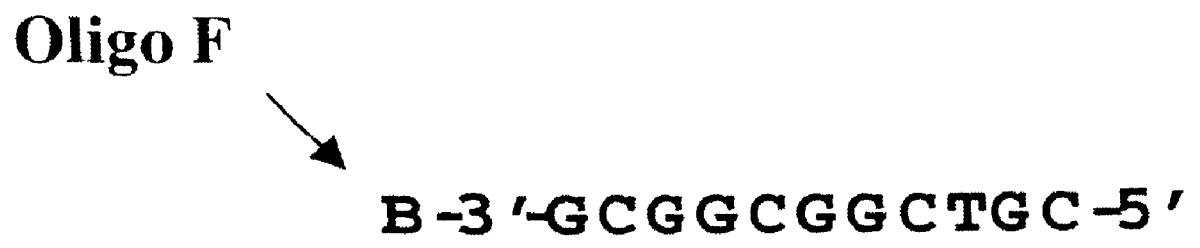

A fourth Oligonucleotide is synthesized which bears a blocked 3' end, by conventional methods of DNA synthesis ("Oligo F," see, FIG. 22). Oligo F is also designed to be complementary to both Oligo D and Oligo G, such that the three Oligonucleotides together form the hybridized structure illustrated in FIG. 23, in which a junction between the two double-stranded regions positions the 5' phosphate group of Oligo G immediately adjacent to the 3' hydroxyl group of Oligo D. In this orientation, Oligo D and Oligo G can be ligated into a single MB component. The 3' blockage of Oligo F can be achieved by various methods, such as the addition of a 3' phosphate group or the use of a 3' dideoxynucleotide. The functional requirement of such a blockage is merely that it prevents Oligo F from taking part in any ligation reactions. Oligo F does not carry a 5' phosphate group, and therefore will not take part in ligation reactions at its 5' end.

Figure 24:
FIG. 24 is a schematic of a sequence of Oligo I.
Figure 25:
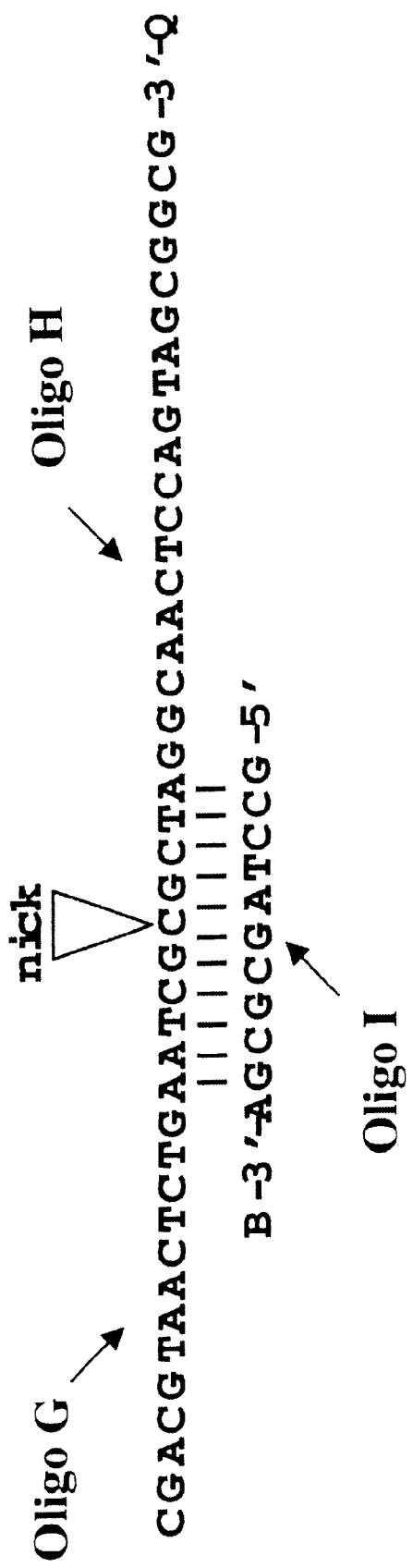
FIG. 25 is a schematic showing hybridization of Oligos G, H and I comprising partial components and a ligation template for the assembly of the example MB.

A fifth Oligonucleotide is synthesized which typically bears a blocked 3' end (e.g., by incorporation of a dideoxy oligo at the 3' end), by conventional methods of DNA synthesis ("Oligo I," see, FIG. 24). Oligo I is also designed to be complementary to both Oligo G and Oligo H, such that the three Oligonucleotides together form the hybridized structure illustrated in FIG. 25, in which a junction between the two double-stranded regions positions the 5' phosphate group of Oligo H immediately adjacent to the 3' hydroxyl group of Oligo G. In this orientation, Oligo G and Oligo H can be ligated into a single MB component. The 3' blockage of Oligo I can be achieved by various methods, such as the addition of a 3' phosphate group or the use of a 3'dideoxy-nucleotide. The functional reason for the blockage is merely that it prevent Oligo I from taking part in any ligation reactions. Oligo I does not carry a 5' phosphate group, and therefore will not take part in ligation reactions at its 5' end.

Figure 26:
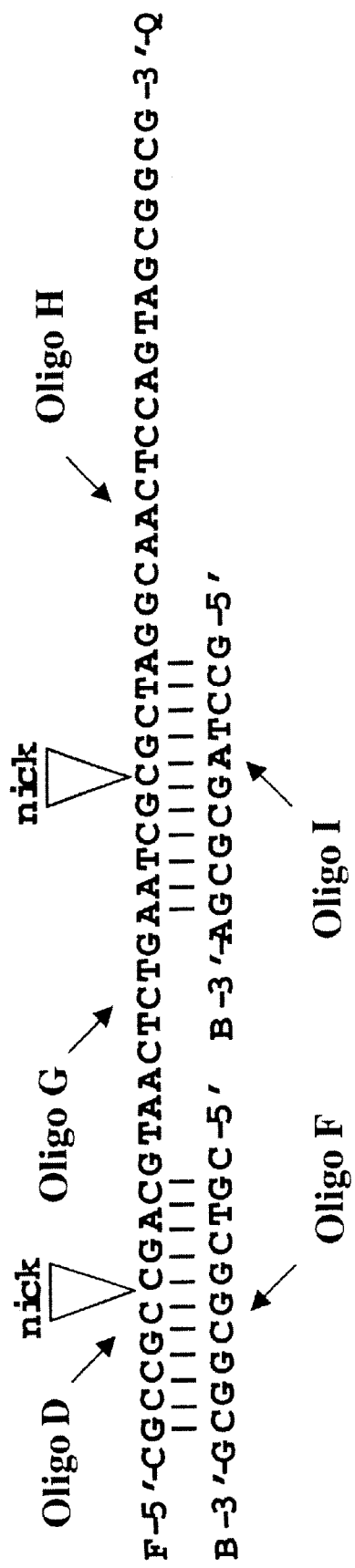
FIG. 26 is a schematic showing hybridization of Oligos D, F, G, H and I comprising partial components and a ligation templates for the assembly of the example MB.

Oligonucleotides D, F, G, H, and I are annealed in a single reaction to generate the structure shown in FIG. 26.

Figure 27:
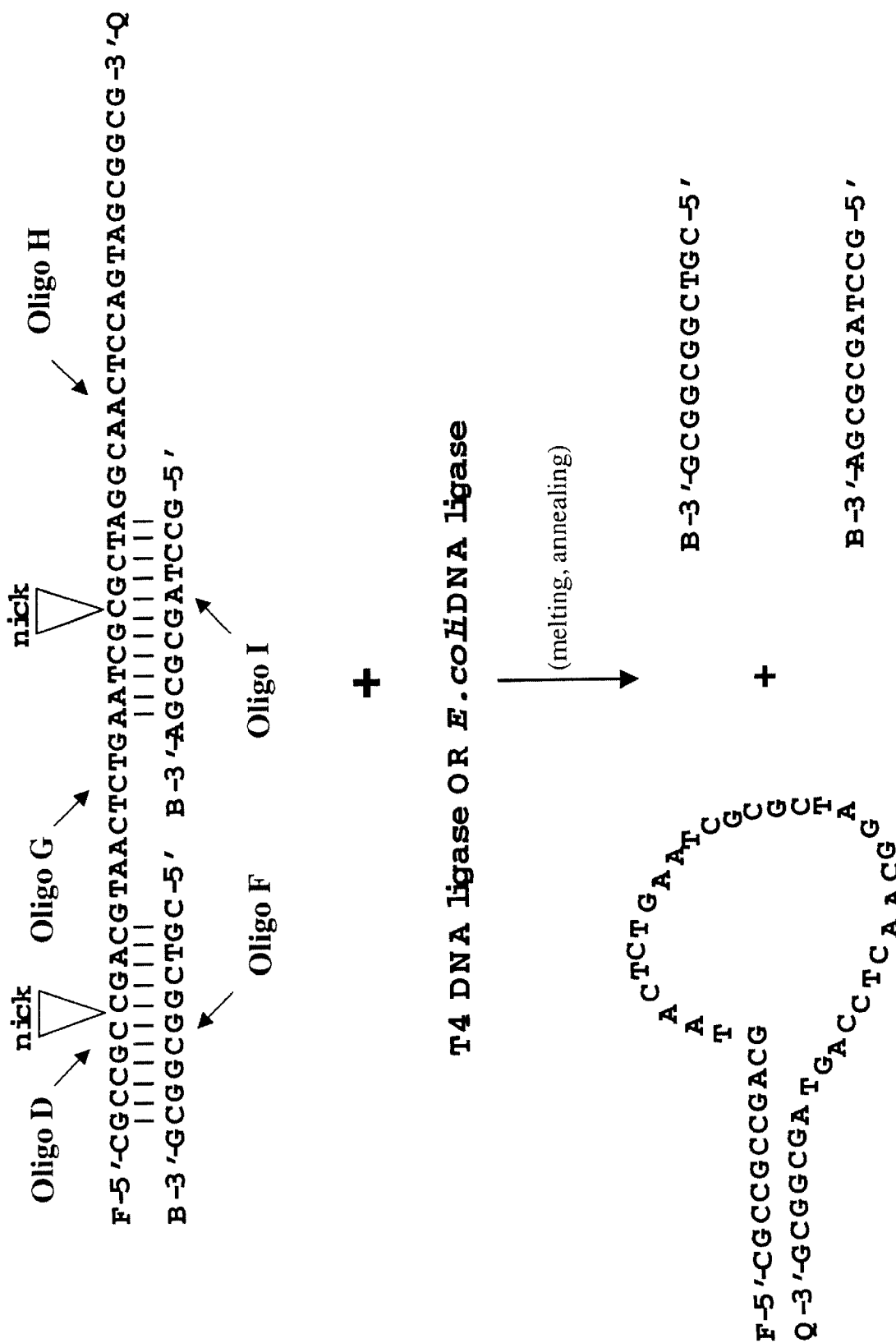
FIG. 27 is a schematic of the conversion of the hybridized five oligo structure in FIG. 26 into the example MB.

Enzymatic ligation, using a enzyme such as T4 ligase or E. coli ligase or any other enzyme capable of ligating nicks in double-stranded DNA molecule, is then used to convert the hybridized structure composed of Oligo D, Oligo F, Oligo G, Oligo H, and Oligo I into three Oligonucleotides (MB, D, G, H and the "ligation template Oligos" F and I), as shown in FIG. 27. Oligo D and Oligo H are designed such that they form a complementary hybrid at their 5' (Oligo D) and 3' (Oligo H) ends, which form the stem of the MB, as illustrated in FIG. 27 in such a way that the fluorophore and quencher molecule are situated at the blunt end of the double-stranded stem to minimize the distance between the two molecules and thereby maximize the quenching of the fluorophore by the quencher. Temperatures and salt concentrations of the ligation reaction are maintained such that the complementary overhangs are kept in close proximity. Conditions of ligation can be manipulated in various ways known to those skilled in the art for maximizing the efficiency of the reaction.

The ligated structure is purified away from the individual unligated components. The ligated structure is also purified away from the excess of Oligos F and I, which is easily achieved due to its greater length. Purification can be achieved either by reverse-phase HPLC, or by any other available method, including, e.g., gel filtration, ion exchange chromatography, or by other means known to those skilled in the art.

The full-length molecular beacon can be used to identify any two nucleic acid sequences that are joined together, whether they be natural or synthetic, by mechanisms that include splicing (e.g., as in RNA splicing), ligation (e.g., as in cloning), PCR, hybridization, annealing, polymerization or by other means known to those skilled in the art.

Figure 28:
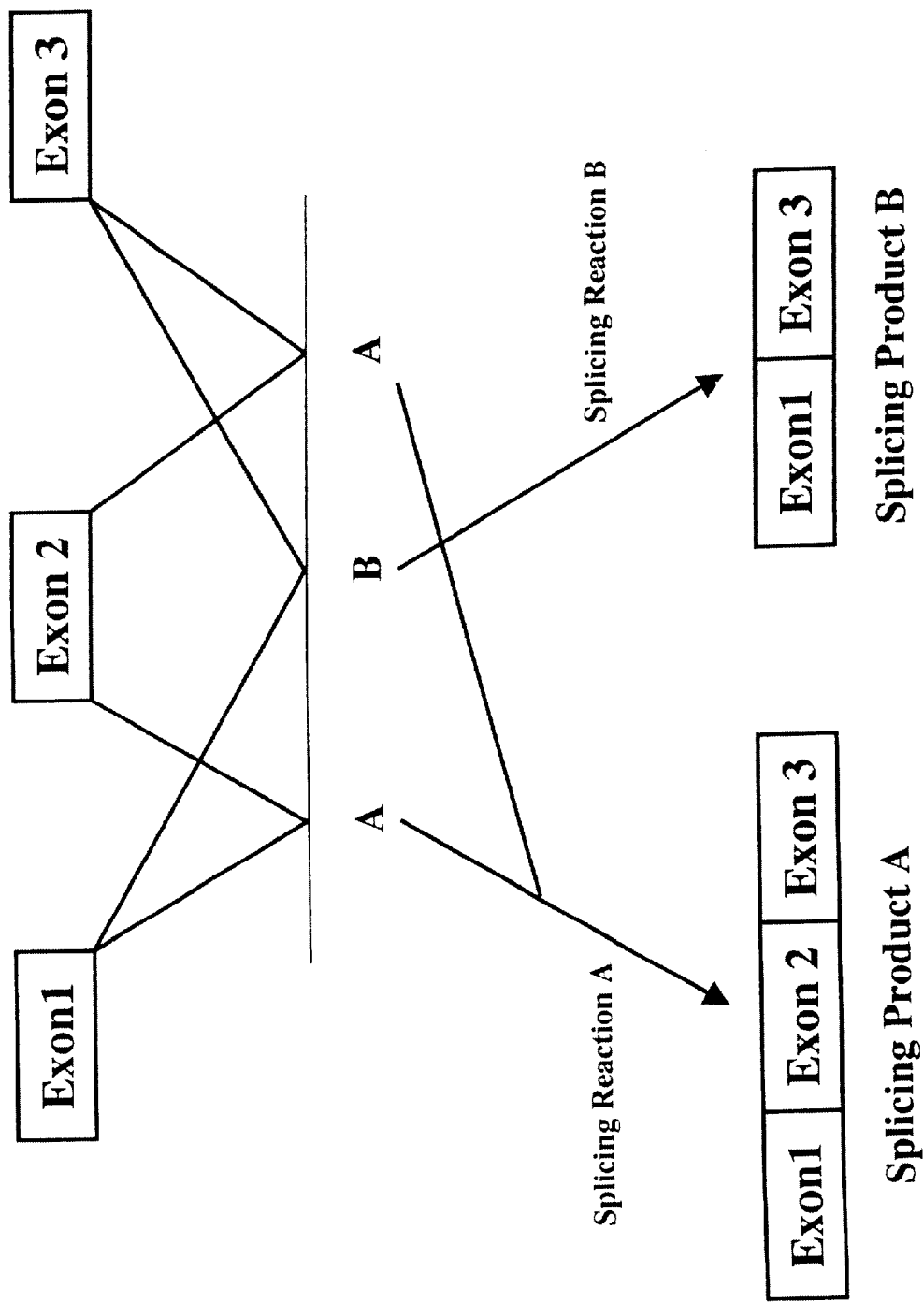
FIG. 28 is a schematic of two alternative splicing reactions.

FIG. 28 illustrates one example of detection of juxtaposed sequences. The example relates to detection of two alternative splicing events, A and B, that generate two different junctions. Splicing reaction A joins exons 1, 2 and 3. Splicing reaction B joins exons 1 and 3.

Figure 29:
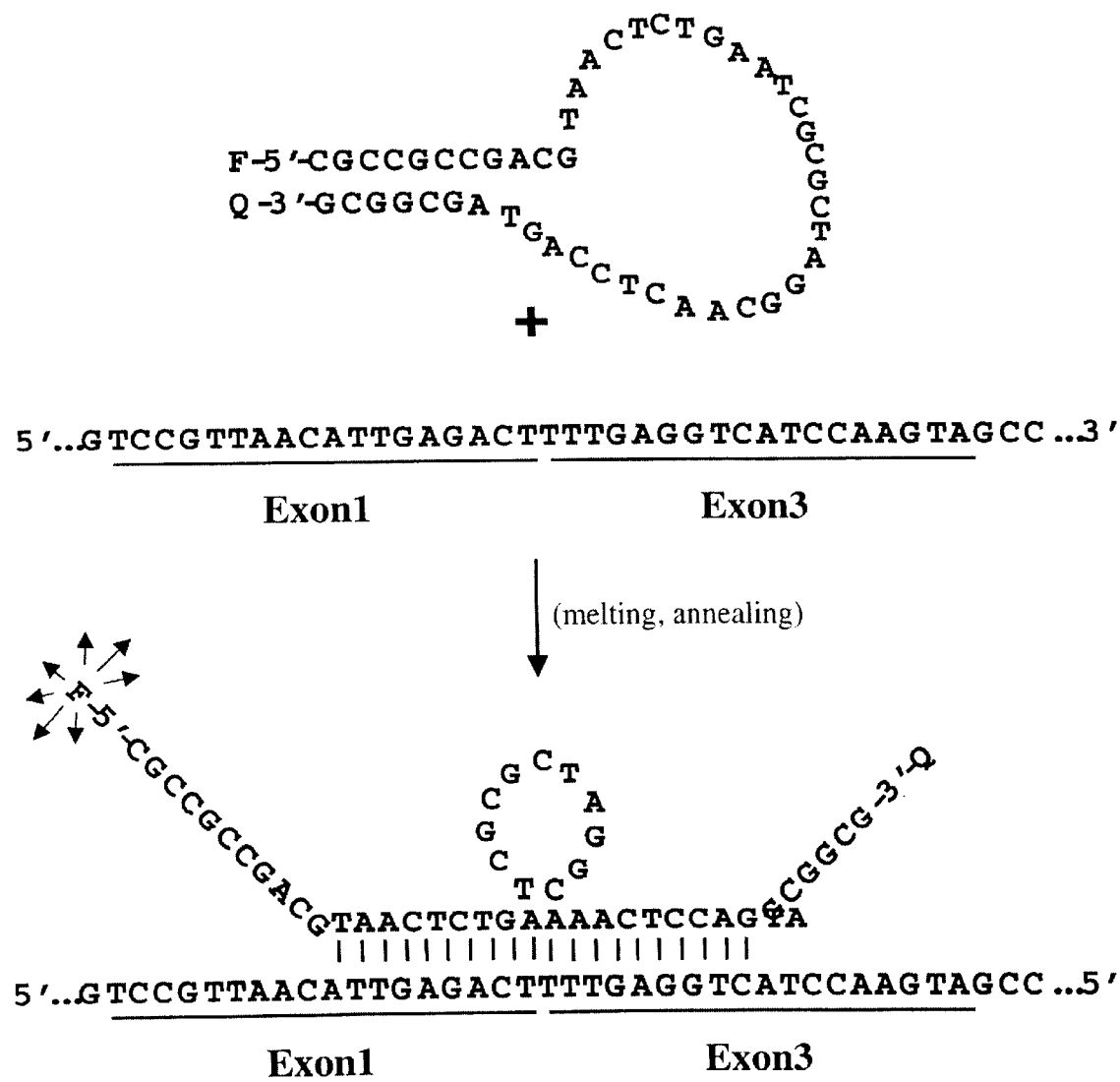
FIG. 29 is a schematic of a general scheme depicting hybridization of the example MB to exon junction target sequences.

Illustrated in FIG. 29 is the annealing of a MB to a target sequence after melting and annealing using optimized temperatures and salt concentrations. The annealing is performed at an optimal stringency to provide for the specific annealing of the MB to both exons. The annealed MB results in a fluorescent emission. The conditions can be manipulated in various ways known to those skilled in the art for maximizing the efficiency of the reaction. The target is composed of sequence from the 3' end of exon 1 and sequence from the 5' end of exon 3. The MB anneals to both exon 1 and exon 3 target sequences, generating a central loop that contains unhybridized template ligation sequence.

This example is shown to illustrate that MBs containing sequences complementary to two (or, optionally, more) different target sequences can be used to identify splicing variants, or any other composite nucleic acid sequences that are complementary to the sequences flanking the template ligation sequence. These include cloned sequences, ligated sequences, spliced sequences and any others known in the art.

Advantages of this approach include the following. First, modular synthesis of MBs can be used to join any two (or more) combinations of sequences together without the need to re-synthesize entire MBs from scratch for each potential target to be detected. Second, synthesis of MBs with two (or more) regions of target sequence complementarity permits the identification of specific splice variants for any given gene. Third, syntheses of MBs with two regions of target sequence complementarity permits the detection of vector and insert sequences at junctions in cloning reactions.

MONITORING REACTIONS

In the methods noted above, the efficiency of ligation reactions is monitored by measuring fluorescence or other relevant MB label properties. This can be performed by any available method e.g., spectrophotometrically, optically, via microscopy, or the like. Common detectors appropriate to such methods include spectrophotometers, CCD arrays, photo multiplier tubes, photodiodes, scanning detectors, microscopes, galvo-scanns and the like. The detector can interface with the system or device for detection regardless of what fluid handling system is used to perform the ligation reactions. Thus, whether the reactions are performed in test tubes, cuvettes, microtiter trays or in microscale systems, detectors are commonly available that can be used to detect photon (or other) signal properties for a reaction system. Devices/systems of the invention can include a detector proximal to a ligation reaction region, or proximal to a hybridization reaction region of the device. Such reaction/hybridization regions include high-throughput reaction regions such as microtiter trays (e.g., 96, 384 or more well trays), container handling systems (e.g., which robotically handle trays, test tubes, or the like), microfluidic devices, or the like. The detection system is typically coupled to a computer, optionally via an analog to digital or digital to analog converter, for transmitting detected signal data to a computer for analysis, storage and data manipulation.

Figure 30:
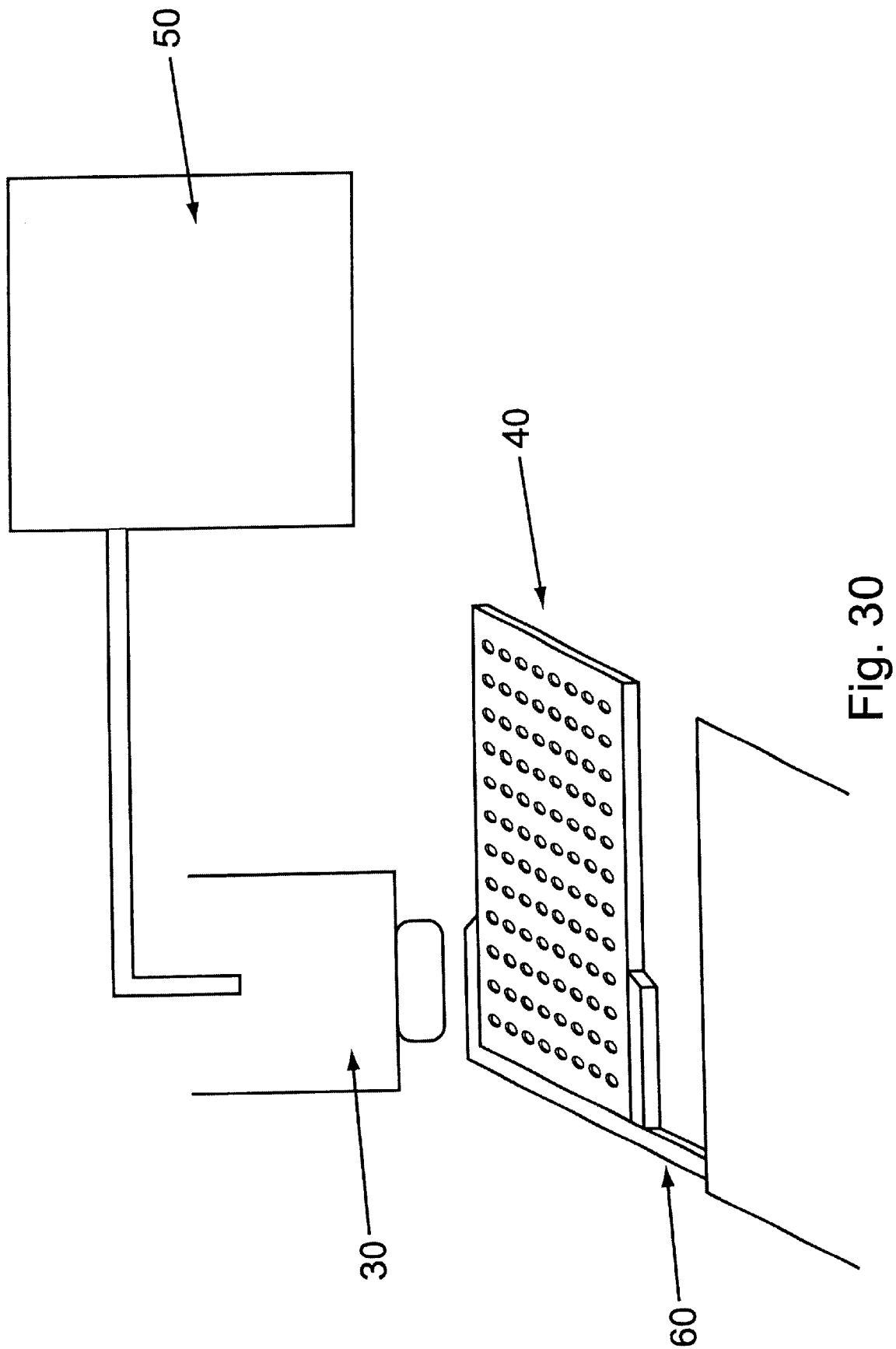
FIG. 30 is a schematic of a detection apparatus for detecting signals, e.g., from one or more ligation mixtures.

In one aspect, the invention provides a device, e.g., which includes a reaction region and a ligation mixture as described herein. The reaction region is commonly part of a high-throughput fluid handling system, such as a microtiter tray or a microfluidic component. The device optionally includes a detector proximal to the reaction region, i.e., any detector as noted above. The device further optionally includes robotics for moving microtiter trays or other fluid containers, one or more computers for controlling the device or receiving and analyzing data from the detector, or the like. FIG. 30 schematically depicts such a device, i.e., having detector 30 proximal to microtiter tray 40. The device/system is shown operably coupled to computer 50 and having robotic armature 50 for manipulating tray 40. Ligation or hybridization mixtures are formed in tray 40 in this embodiment.

A variety of configurations of these basic elements can be used to form a system or device of the invention.

MB COMPONENT SYNTHESIS

MB components (oligos, including those labeled with fluorophores or quenchers) can be synthesized using conventional methods. For example, oligos or PNAs can be synthesized on commercially available automated oligonucleotide/PNA synthesis machines using standard methods. Labels can be attached to the oligos or PNAs either during automated synthesis or by post-synthetic reactions which have been described before see, e.g., Tyagi and Kramer (1996) "Molecular beacons: probes that fluoresce upon hybridization" *Nature Biotechnology* 14:303–308 and U.S. Pat. No. 6,037,130 to Tyagi et al (Mar. 14, 2000), entitled "Wavelength-shifting probes and primers and their use in assays and kits." and U.S. Pat. No. 5,925,517 (Jul. 20, 1999) to Tyagi et al. entitled "Detectably labeled dual conformation oligonucleotide probes, assays and kits." Additional details on synthesis of functionalized oligos can be found in Nelson, et al. (1989) "Bifunctional Oligonucleotide Probes Synthesized Using A Novel CPG Support Are Able To Detect Single Base Pair Mutations" *Nucleic Acids Research* 17:7187–7194.

Labels/quenchers can be introduced to the oligonucleotides or PNAs, e.g., by using a controlled-pore glass column to introduce, e.g., the quencher (e.g., a 4-dimethylaminoazobenzene-4'-sulfonyl moiety (DABSYL). For example, the quencher can be added at the 3' end of oligonucleotides during automated synthesis; a succinimidyl ester of 4-(4'-dimethylaminophenylazo) benzoic acid (DABCYL) can be used when the site of attachment is a primary amino group; and 4-dimethylaminophenylazophenyl-4'-maleimide (DABMI) can be used when the site of attachment is a sulphydryl group. Similarly, fluorescein can be introduced in the oligos, either using a fluorescein phosphoramadite that replaces a nucleoside with fluorescein, or by using a fluorescein dT phosphoramadite that introduces a fluorescein moiety at a thymidine ring via a spacer. To link a fluorescein moiety to a terminal location, iodoacetoamidofluorescein can be coupled to a sulphydryl group. Tetrachlorofluorescein (TET) can be introduced during automated synthesis using a 5'-tetrachloro-fluorescein phosphoramadite. Other reactive fluorophore derivatives and their respective sites of attachment include the succinimidyl ester of 5-carboxyrhodamine-6G (RHD) coupled to an amino group; an iodoacetamide of tetramethylrhodamine coupled to a sulphydryl group; an isothiocyanate of tetramethylrhodamine coupled to an amino group; or a sulfonylchloride of Texas red coupled to a sulphydryl group. During the synthesis of these labeled components, conjugated oligonucleotides or PNAs can be purified, if desired, e.g., by high pressure liquid chromatography or other methods.

In general, synthetic methods for making oligonucleotides and PNAs (including labeled oligos and PNAs) is well known. For example, oligonucleotides can be synthesized chemically according to the solid phase phosphoramidite triester method described by Beaucage and Caruthers (1981), *Tetrahedron Letts.*, 22(20):1859–1862, e.g., using a commercially available automated synthesizer, e.g., as described in Needham-VanDevanter et al. (1984) *Nucleic Acids Res.*, 12:6159–6168. Oligonucleotides, including modified oligonucleotides can also be ordered from a variety of commercial sources known to persons of skill. There are many commercial providers of oligo synthesis services, and thus, this is a broadly accessible technology. Any nucleic acid can be custom ordered from any of a variety of commercial sources, such as The Midland Certified Reagent Company (mcrc@oligos.com), The Great American Gene Company (www.genco.com), ExpressGen Inc. (www.expressgen.com), Operon Technologies Inc. (Alameda, Calif.) and many others. Similarly, PNAs can be custom ordered from any of a variety of sources, such as PeptidoGenic (pkim@ccnet.com), HTI Bio-products, inc. (www.htibio.com), BMA Biomedicals Ltd (U.K.), Bio-Synthesis, Inc., and many others.

LIGATION OF OLIGONUCLEOTIDES AND PNAS

A number of approaches are available for the ligation of oligonucleotides, PNAs and even for ligation of PNAs to oligonucleotides. Thus, the MBs of the invention can be formed from PNAs, oligonucleotides, or both PNAs and oligonucleotides. Ligation, as used in this context, simply refers to producing a covalent bond between the two or more elements to be ligated.

Ligation of nucleic acids by enzymatic approaches is well known. The basic enzymes and reaction conditions for ligation can be found in any of a variety texts, including, e.g., Berger and Kimmel (1989), *Guide to Molecular Cloning Techniques, Methods in Enzymology* volume 152 Academic Press, Inc., San Diego, Calif. (Berger); Sambrook et al., *Molecular Cloning—A Laboratory Manual* (2nd Ed.), Vol. 1–3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 2000) ("Ausubel")). Oligonucleotide-PNA chimeras can also be made. See, Koppitz, M., Nielsen P. E. & Orgel, L. (1997) Formation of oligonucleotide-PNA-Chimeras by Template-directed Ligation. J. Amer. Chem. Soc. 120, 4563–4569.

Ligation of nucleic acids via chemical approaches also uses any of a variety of well known chemistries. Chemical ligation can involve use of reactive groups on the molecules to be ligated, such as hydroxyl, phosphate, sulfhydryl, amino, alkyl phosphate, alkyl amino or hydroxy alkyl groups. Covalently reactive groups are preferred. Examples of the basic chemistry relevant to chemical ligation include Stryer (1988) Biochemistry, third edition (or later editions) Freeman and Co. New York, N.Y.; Pine et al. *Organic Chemistry Fourth Edition* (1980) McGraw-Hill, Inc. (USA) (or later editions); March, *Advanced Organic Chemistry Reactions Mechanisms and Structure* 4th ed J. Wiley and Sons (New York, N.Y., 1992) (or later editions); Greene, et al., *Protective Groups In Organic Chemistry*, 2nd Ed., John Wiley & Sons, New York, N.Y., 1991 (or later editions); Lide (ed) (1995) *The CRC Handbook of Chemistry and Physics* 75th edition (or later editions); and in the references cited in the foregoing.

Chemistries for joining short oligonucleotides (e.g., trinucleotides) are especially well known and can be adapted to the present invention to chemically join longer oligonucleotides. References that show chemical linkage of short oligos include Virnekäs, B., et al., (1994) *Nucleic Acids Res.*, 22, 5600–5607; Kayushin, A. L. et al., (1996) *Nucleic Acids Res.*, 24, 3748–3755, Huse, U.S. Pat. No. 5,264,563 "Process For Synthesizing Oligonucleotides With Random Codons," Lyttle et al., U.S. Pat. No. 5,717,085 "Process For Preparing Codon Amidites," Shortle et al., U.S. Pat. No. 5,869,644 "Synthesis Of Diverse And Useful Collections Of Oligonucleotides," Greyson, U.S. Pat. No. 5,789,577 "Method For The Controlled Synthesis Of Polynucleotide Mixtures Which Encode Desired Mixtures Of Peptides," and Huse, WO 92/06176 "Surface Expression Libraries Of Randomized Peptides."

DONORS AND ACCEPTORS (FLUOROPHORES AND QUENCHERS) IN MBS

In MBs, a central target-recognition sequence is flanked by arms that hybridize to one another when the probe is not hybridized to a target strand, forming a "hairpin" structure, in which the target-recognition sequence (which is sometimes referred to as the "probe sequence") is in the single-stranded loop of the hairpin structure, and the arm sequences form a double-stranded stem hybrid.

Operation of the MB is rather straightforward. When the probe hybridizes to a target, a relatively rigid helix is formed, causing the stem hybrid to unwind and forcing the arms of the MB apart. A label/quencher pair, such as the fluorophore EDANS and the quencher DABCYL, are attached to the arms, e.g., by alkyl spacers. When the MB is not hybridized to a target strand, the fluorophore's emission is quenched. When the Molecular Beacon is hybridized to a target strand, the FRET pair is separated by more than 100 angstroms, and the fluorophore's emission is not quenched. Thus, emitted fluorescence signals the presence, in real time, of target strands being hybridized to the MB.

Molecular beacon probes can have target recognition sequences of typically about 7–140 nucleotides in length and arms that form a stem hybrid, or "stem duplex" of about 3–25 nucleotides in length. Modified nucleotides and modified nucleotide linkages may be used for MB construction, even including, e.g., peptide nucleic acid ("PNAs").

FRET Probes

As noted, MBs made according to the present invention can utilize FRET to detect nucleic acid hybridization. Fluorescence resonance energy transfer (FRET) is a distance-dependent interaction between the electronic excited states of two molecules (e.g., a fluorophore and a quenching molecule) in which excitation is transferred from a donor molecule (the fluorophore in this example) to an acceptor molecule (the quenching molecule in this example) typically without any photon emission. FRET is dependent on an inverse sixth power of the separation of the donor and acceptor moieties, making it useful over distances comparable with the dimensions of biological macromolecules.

The primary conditions for typical FRET are well known and can be used in the design and construction of MBs of the invention. First, donor and acceptor molecules are in close proximity (typically 10–100 Å) for FRET to occur. Second, the absorption spectrum of the acceptor typically overlaps the fluorescence emission spectrum of the donor. Third, donor and acceptor transition dipole orientations are usually approximately parallel.

As noted, MBs can incorporate any of a variety of fluorophore/quencher (in this context, "donor/acceptor") combinations. With regard to such pairs, there are a number of fluorophores which are known to quench one another. Examples of interactive fluorescent label pairs include terbium chelate and TRITC (tetrarhodamine isothiocyanate), europium cryptate and Allophycocyanin, Fluorescein and Tetramethylrhodamine, IAEDANS and Fluorescein, EDANS and DABCYL, Fluorescein and Fluorescein, BODIPY FL and BODIPY FL, and Fluorescein and QSY 7 dye.

Fluorescence quenching is a bimolecular process that reduces the fluorescence quantum yield, typically without changing the fluorescence emission spectrum. Quenching can result from transient excited state interactions, (collisional quenching) or, e.g., from the formation of non-fluorescent ground state species. Self quenching is the quenching of one fluorophore by another; it tends to occur when high concentrations, labeling densities, or proximity of labels occurs. Fluorescent resonance energy transfer (FRET) is a distance dependent excited state interaction in which emission of one fluorophore is coupled to the excitation of another which is in proximity (close enough for an observable change in emissions to occur).

In some applications, the donor and acceptor moieties are different, in which case MB hybridization is detected by the appearance of sensitized fluorescence of the acceptor (or even by quenching of donor fluorescence, i.e., in the context of the invention by measuring elimination of fluorescence by elimination of target-specific hybridization). When the donor and acceptor are the same, FRET can be detected by fluorescence depolarization.

Nonfluorescent acceptors such as DABCYL and QSY 7 and QSY 33 dyes have the particular advantage of eliminating background fluorescence resulting from direct (i.e., nonsensitized) acceptor excitation. A variety of probes incorporating fluorescent donor-nonfluorescent acceptor combinations have been developed for detection of nucleic acid hybridization events. See also, Haugland (1996) Handbook of Fluorescent Probes and Research Chemicals Published by Molecular Probes, Inc., Eugene, Oreg. e.g., at chapter 13) or a more current on-line (www.probes.com) or CD-ROM version of the Handbook (available from Molecular Probes, Inc.).

Non-FRET Based Quenchers in MBs

An alternate to the use of FRET probes in the context of MBs is found in U.S. Pat. No. 6,150,097 to Tyagi et al (Nov. 21, 2000) entitled "Nucleic acid detection probes having non-FRET fluorescence quenching and kits and assays including such probes." Instead of using donor-acceptor moieties that follow the typical rules of FRET, MBs can bring the fluorophore and quencher into very close contact, resulting in quenching regardless of whether FRET occurs. That is, when attached to a MB such that it is in contact with, or "touching", the first fluorophore in one of its conformations, a quenching moiety need not have an absorption spectrum that overlaps the emission spectrum of the first fluorophore. Furthermore, the absorption wavelength of the quencher can be shorter than the fluorophore's excitation maximum and emission wavelength. Similarly, a second fluorophore that absorbs at a wavelength shorter than the emission wavelength of the first can, in the probe construction described above, act as a quencher; that is, suppress emission by the first fluorophore and dissipate the incident energy as heat rather than as photon emission.

In probes constructed according to these methods, changes in the absorption spectra of the label pair can be used as a detectable signal, rather than simply monitoring a change in fluorescence. When a change in absorption is utilized, the label pair may include any two chromophores, that is, fluorophores, quenchers and other chromophores. The label pair can even include identical chromophores or fluorophores. Thus, for example, DABCYL, when attached to one end of a Molecular Beacon, can effectively quench fluorophores attached to the other end of the MB. This is in violation of standard FRET rules, enlarging the available number of fluorophore-quencher pairs that can be used in MBs beyond those available for FRET.

LIBRARIES OF MB COMPONENTS AND LIGATION MIXTURES

One aspect of the invention is the construction of libraries of MB components which can be ligated according to the methods herein. The libraries include a set of a hairpin loop oligonucleotides or PNAs, each of which includes a subsequence of at least one molecular beacon (but less than all of the final product MB). These oligos are typically arrayed or stored in an otherwise accessible format. For example, the oligos can be arrayed on a microtiter tray. Other components can be added to the array members, including the addition of at least one label or label quenching oligonucleotide or PNA (i.e., an oligonucleotide which includes a label or a label quencher). Ligation of at least one hairpin oligonucleotide or PNA and the label or label quenching oligonucleotide or PNA produces a molecular beacon or molecular beacon subsequence-and thus an array of MBs.

In one embodiment, the array of MBs includes oligos which are systematically varied with respect to the loop or stem regions, i.e., each differing by one or a few monomer units (nucleotides, PNA monomers, etc.). MB synthesis and hybridization properties are monitored in real time, facilitating selection of sequences with optimal MB synthesis properties, and/or having optimal hybridization properties for one or more target.

In other embodiments, the arrays are designed to optimize other MB parameters such as multiplexing capabilities. Multiplexed detection schemes (e.g., simultaneously monitoring different hybridization events by monitoring different labels in a single solution) are of increasing value generally. Thus, the present invention's ability to optimize properties in an array based format provides a mechanism for simultaneously optimizing one or more than one variable across a population of MBs or MM synthesis schemes.

As noted, members of the library can be located in a microtiter tray or other array, with individual members types of the hairpin loop oligonucleotides or PNAs being located in wells of the microtiter tray. The wells (or other array containing compartments), can further include components relevant to MB synthesis or activity, including ligases, ligation buffers, the label or label quenching oligonucleotide or PNA, target nucleic acids, or the like.

SYSTEMS COMPRISING OLIGOS, LIGATION COMPONENTS AND SEQUENCE INFORMATION

In one aspect, the invention includes systems for the design and synthesis of the MBs according to the methods herein. The system can include, e.g., a computer with appropriate software for manipulating text strings corresponding to oligos or PNAs to be synthesized, software for modeling MB hybridization to a target, etc. Similarly, the system can include an automated synthesizer coupled to the computer (directly or indirectly, e.g., through a cable, LAN or across the internet) for synthesizing oligos corresponding to the character strings in the computer.

The computer typically includes appropriate software for receiving user instructions, either in the form of user input into a set parameter fields, e.g., in a GUI, or in the form of preprogrammed instructions, e.g., preprogrammed for a variety of different specific operations. The software optionally converts these instructions to appropriate language for instructing the operation of the synthesizer to carry out the desired synthetic operation. The computer can also receives data from the synthesizer regarding yield, cycle completion or the like and can interpret the data, provide it to a user in a human readable format, or can use that data to initiate further synthetic operations, in accordance with any programming by the user.

KITS

The present invention can include kits that include any of the components of the compositions, systems, ligation mixtures or libraries herein. Typically, the kits further include features that are relevant to the distribution of such materials, including packaging materials, instructions for using the components to produce one or more molecular beacons, one or more containers for holding the components, or the like.

In addition, components providing positive or negative controls for any reaction relevant to the synthesis or use of a molecular beacon can be provided. These include standards for calibrating any MB synthesis or detection reaction, standard target sequences (e.g., positive or negative controls that are known to bind or to not bind to the MB at issue), or the like. In addition, auxiliary components relevant to any MB detection reaction can be included, such as amplification primers for amplifying a target sequence (e.g., via PCR or LCR) can be included.

While the foregoing invention has been described in some detail for purposes of clarity and understanding, it will be clear to one skilled in the art from a reading of this disclosure that various changes in form and detail can be made without departing from the true scope of the invention. For example, all the techniques and compositions described above may be used in various combinations. All publications, patent applications, patents and/or other documents cited in this application are incorporated by reference in their entirety for all purposes to the same extent as if each individual publication or patent document were individually so denoted.

What is claimed is:

1. A method of making one or more molecular beacons or molecular beacon components, comprising:
   providing a first oligonucleotide or peptide nucleic acid (PNA) corresponding to a first subsequence of a molecular beacon;
   providing a second oligonucleotide or PNA corresponding to a second subsequence of the molecular beacon;
   providing a third oligonucleotide or PNA corresponding to a third subsequence of the molecular beacon; and,
   ligating the first, second and third oligonucleotides or PNAs together, thereby forming the molecular beacon or the molecular beacon component wherein the first, second and third oligonucleotides are ligated using two template oligonucleotides to align the first, second and third oligonucleotides for ligation.

2. The method of claim 1, comprising monitoring a ligation-dependent change in a signal output of the molecular beacon, the molecular beacon component, the first oligonucleotide or PNA, or the second oligonucleotide or PNA, or the third oligonucleotide or PNA, wherein the ligation-dependent signal output is a change in a fluorescence emission at a hybridization temperature that permits intra-molecular hybridization of the molecular beacon.

3. The method of claim 1, further comprising optimizing one or more reaction parameters to increase yield of the molecular beacon or molecular beacon component or efficiency of the ligating step.

4. The method of claim 1, further comprising optimizing one or more reaction parameters to minimize an amount of unligated material remaining following the ligating step.

5. The method of claim 1, further comprising monitoring one or more melting and annealing reactions by monitoring one or more intra-molecular melting or intra-molecular annealing dependent reactions.

6. The method of claim 5, comprising identifying one or more molecular beacon that has an opted loop sequence.

7. The method of claim 1, wherein the first oligonucleotide or PNA comprises a label moiety and the second oligonucleotide comprises a label quenching moiety.

8. The method of claim 7, wherein the label moiety is selected from the group consisting of: Texas red, terbium chelate, europium cryptate, DABCYL, Fluorescein, IAEDANS, EDANS, and BODIPY FL.

9. The method of claim 7, wherein the quenching moiety is selected from the group consisting of: TRITC (tetrarhodamine isothiocyanate), Allophycocyanin, EDANS, Tetramethylrhodamine, DABCYL, Fluorescein, BODIPY FL, and QSY 7 dye.

10. The method of claim 1, comprising monitoring a ligation-dependent change in a signal output of the molecular beacon, the molecular beacon component, the first oligonucleotide or PNA, or the second oligonucleotide or PNA, or the third oligonucleotide or PNA.

11. The method of claim 1, wherein the first, second and third oligonucleotides are complementary to two or more proximal subsequences in a target nucleic acid.

12. The method of claim 1, wherein the first, second and third oligonucleotides are complementary to two or more proximal subsequences in a target nucleic acid, wherein the subsequences are made proximal in the target nucleic acid by splicing or ligating the subsequences together.

13. The method of claim 1, wherein the first and second oligonucleotides or PNAs are aligned on a template nucleic acid prior to said ligating step.

14. The method of claim 13, wherein the template nucleic acid is a synthetic single-stranded oligonucleotide.

15. The method of claim 1, wherein the ligating step is performed via enzymatic ligation.

16. The method of claim 15, wherein the ligating step is performed using a ligase enzyme selected from the group consisting of: a Taq DNA ligase, an *E. coli* DNA ligase, and a T4 DNA ligase.

17. The method of claim 1, wherein the ligating step is performed via chemical ligation.

18. The method of claim 1, further comprising purifying the molecular beacon from one or more unligated first or second or third oligonucleotides or PNAs.

19. The method of claim 18, wherein the molecular beacon is purified from the unligated first or second or third oligonucleotides or PNAs using HPLC.

20. A device comprising:
   a reaction region comprising a ligation mixture therein, the ligation mixture comprising a first oligonucleotide or PNA comprising a label moiety; a second oligonucleotide or PNA comprising a quenching moiety that quenches the label moiety when placed proximal to or in contact with the label moiety; and a third oligonucleotide or PNA;
   wherein ligation of the first, second and third oligonucleotides or PNAs results in formation of a molecular beacon and wherein the ligation mixture further comprises fourth and fifth oligonucleotides which provide templates for ligation of the first, second and third oligonucleotides;
   a ligase; and,
   a detector proximal to the reaction region, which detector detects one or more ligation-dependent change in an output of the label moiety.

21. The device of claim 20, wherein the first and second oligonucleotides or PNAs are at least partly complementary.

22. The device of claim 20, wherein, upon ligation, nucleotides of the first and second oligonucleotides form at least a portion of a molecular beacon stem and nucleotides of the third oligonucleotide forms at least portion of a hairpin loop portion of the molecular beacon.

23. The device of claim 20, wherein the label or quenching moiety is selected from the group consisting of: Texas red, terbium chelate, europium cryptate, DABCYL, Fluorescein, IAEDANS, EDANS, and BODIPY FL.

24. The device of claim 20, wherein the label or quenching moiety is selected from the group consisting of: TRITC (tetrarhodamine isothiocyanate), Allophycocyanin, EDANS, Tetramethylrhodamine, DABCYL, Fluorescein, BODIPY FL, and QSY 7 dye.

25. The device of claim 20, wherein the ligase is selected from the group consisting of: E. coli ligase, T4 ligase, and Taq ligase.

26. The device of claim 20, further comprising a ligation buffer.

27. The device of claim 20, wherein the second oligonucleotide or PNA is at least partly complementary to one or more target nucleic acid.

28. The device of claim 20, wherein the second oligonucleotide or PNA is at least partly complementary to one or more single nucleotide polymorphism.

29. A kit comprising each of the components of the ligation mixture of claim 20.

30. The kit of claim 29, further comprising one or more of: packaging materials, instructions for using the components to produce one or wore molecular beacons, one or more containers for holding the components, standards for calibrating any molecular beacon detection reaction, standard target sequences, or amplification primers for amplifying a target sequence.

31. A library of molecular beacon components, comprising:
a set of a plurality of hairpin loop oligonucleotides or PNAs, each of the plurality of hairpin loop oligonucleotides or PNAs comprising a subsequence of at least one molecular beacon, the subsequence comprising less than all of the molecular beacon;
at least one first label and at least one first label quenching oligonucleotide or PNA, which first label and first label quenching oligonucleotides or PNAs each comprise at least one label or label quenching moiety and
at least two template oligonucleotides, which at least two template oligonucleotides collectively hybridize to a first of the hairpin loop oligonucleotides, the first or the label quenching oligonucleotides and the first of the label oligonucleotides, wherein ligation of the first hairpin loop oligonucleotide, first label quenching oligonucleotide and first label oligonucleotide, when hybridized to the two template oligonucleotides, produces a molecular beacon.

32. The library of claim 31, wherein the first hairpin loop oligonucleotide or PNA comprises a label or label quenching moiety, and wherein ligation of the fist hairpin loop oligonucleotide or PNA to the first label or first label quenching oligonucleotide or PNA produces a molecular beacon.

33. The library of claim 31, wherein the library is located in a microtiter tray, with individual members types of the hairpin loop oligonucleotides or PNAs being located in wells of the microtiter tray.

34. The library of claim 31, wherein the library is located in a microtiter tray, with individual members types of the hairpin loop oligonucleotides or PNAs being located in wells of the microtiter tray, wherein each well of the tray further comprises one or more of: a ligase, a ligation buffer, a target nucleic acid, or the label or label quenching oligonucleotide or PNA.

35. The library of claim 31, further comprising one or more ligase enzyme.

36. A kit comprising the library of claim 31 and one or more of: packaging materials, instructions for using the library to produce one or more molecular beacons, one or more containers for holding one or more components of the library, one or more ligase enzyme, one or more standard target molecule, one or more amplification oligonucleotides, or one or more ligation buffer.

37. A method of detecting a juxtaposition of two or more target subsequences in a target nucleic acid, comprising:
forming a molecular beacon by ligating first, second and third oligonucleotides together while the first, second and third oligonucleotides are hybridized to first second template oligonucleotides, thereby forming a molecular beacon, wherein the first, second and third oligonucleotides collectively comprise regions of complementarity to first and second target subsequences;
hybridizing the resulting molecular beacon to the target nucleic add; and,
detecting target-specific hybridization of the molecular beacon to the first and second subsequences.

38. The method of claim 37, wherein forming the molecular beacon further comprises purifying the molecular beacon from an unligated first, second or third oligonucleotide.

39. The method of claim 37, wherein the juxtaposed target subsequences are juxtaposed by one or more of: RNA splicing, RNA splicing and reverse transcription, ligation, or PCR.

* * * * *